(12) United States Patent
Saadat et al.

(10) Patent No.: US 7,703,459 B2
(45) Date of Patent: Apr. 27, 2010

(54) APPARATUS AND METHODS FOR MAPPING OUT ENDOLUMINAL GASTROINTESTINAL SURGERY

(75) Inventors: Vahid Saadat, Atherton, CA (US); Chris Rothe, San Mateo, CA (US); Ruey-Feng Peh, Mountain View, CA (US); Richard C. Ewers, Fullerton, CA (US)

(73) Assignee: USGI Medical, Inc., San Clemente, CA (US)

( * ) Notice: Subject to any disclaimer, the term of this patent is extended or adjusted under 35 U.S.C. 154(b) by 1245 days.

(21) Appl. No.: 10/954,658

(22) Filed: Sep. 29, 2004

(65) Prior Publication Data

US 2005/0203500 A1     Sep. 15, 2005

Related U.S. Application Data

(63) Continuation-in-part of application No. 10/797,910, filed on Mar. 9, 2004.

(51) Int. Cl.
*A61B 17/00* (2006.01)
(52) U.S. Cl. .............................. 128/898; 606/1; 606/32; 606/41; 606/45; 606/49; 606/167
(58) Field of Classification Search ................. 128/898; 606/27
See application file for complete search history.

(56) References Cited

U.S. PATENT DOCUMENTS

| | | | |
|---|---|---|---|
| 616,672 A | 12/1898 | Kelling | |
| 1,814,791 A | 7/1931 | Endo et al. | |
| 2,201,610 A | 5/1940 | Dawson, Jr. | |
| 2,413,142 A | 12/1946 | Jones et al. | |
| 2,510,198 A | 6/1950 | Tesmer | |
| 2,533,494 A | 12/1950 | Mitchell, Jr. | |
| 3,060,972 A | 10/1962 | Sheldon | |
| 3,096,962 A | 7/1963 | Meijs | |
| 3,150,379 A | 9/1964 | Brown | |
| 3,162,214 A | 12/1964 | Bazinet, Jr. | |
| 3,166,072 A | 1/1965 | Sullivan, Jr. | |
| 3,168,274 A | 2/1965 | Street | |

(Continued)

FOREIGN PATENT DOCUMENTS

EP     0 480 428 A2     4/1992

(Continued)

OTHER PUBLICATIONS

Angiolink, The Expanding Vascular Staple [brochure], 1 page total.

(Continued)

*Primary Examiner*—Lee S Cohen
(74) *Attorney, Agent, or Firm*—Levine Bagade Han LLP

(57) ABSTRACT

Apparatus and methods are provided for mapping out endoluminal gastrointestinal surgery, including endoluminal gastric reduction. Mapping is achieved by locally marking the interior of the gastrointestinal lumen at specified locations. In some variations, mucosectomy and/or mucosal ablation are performed to map out endoluminal GI surgery, to facilitate direct endoluminal engagement of underlying muscularis tissue and/or to initiate a wound healing response. Specialized apparatus may be provided to achieve desired spacing and/or positioning of tissue markings, as well as to actually form the markings. Methods of using apparatus of the present invention are provided.

23 Claims, 27 Drawing Sheets

U.S. PATENT DOCUMENTS

| | | |
|---|---|---|
| 3,430,662 A | 3/1969 | Guarnaschelli |
| 3,494,006 A | 2/1970 | Brumlik |
| 3,546,961 A | 12/1970 | Marton |
| 3,551,987 A | 1/1971 | Wilkinson |
| 3,646,615 A | 3/1972 | Ness |
| 3,664,345 A | 5/1972 | Dabbs et al. |
| 3,753,438 A | 8/1973 | Wood et al. |
| 3,858,578 A | 1/1975 | Milo |
| 3,867,944 A | 2/1975 | Samuels |
| 3,874,388 A | 4/1975 | King et al. |
| 3,910,281 A | 10/1975 | Kletschka et al. |
| 3,913,565 A | 10/1975 | Kawahara |
| 3,974,834 A | 8/1976 | Kane |
| 3,976,079 A | 8/1976 | Samuels et al. |
| 4,007,743 A | 2/1977 | Blake |
| 4,054,128 A | 10/1977 | Seufert et al. |
| 4,060,089 A | 11/1977 | Noiles |
| 4,069,825 A | 1/1978 | Akiyama |
| 4,245,624 A | 1/1981 | Komiya |
| 4,366,810 A | 1/1983 | Slanetz, Jr. |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,586,503 A | 5/1986 | Kirsch et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,648,733 A | 3/1987 | Merkt |
| 4,655,257 A | 4/1987 | Iwashita |
| 4,669,473 A | 6/1987 | Richards et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,832,055 A | 5/1989 | Palestrant |
| 4,841,888 A | 6/1989 | Mills et al. |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsch et al. |
| 4,949,927 A | 8/1990 | Madocks et al. |
| 4,957,498 A | 9/1990 | Caspari et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Gugliemi et al. |
| 5,123,914 A | 6/1992 | Cope |
| RE34,021 E | 8/1992 | Mueller et al. |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,251,611 A | 10/1993 | Zehel et al. |
| 5,254,126 A | 10/1993 | Filipi et al. |
| 5,261,916 A | 11/1993 | Engelson |
| 5,268,001 A | 12/1993 | Nicholson et al. |
| 5,282,827 A | 2/1994 | Kensey et al. |
| 5,284,488 A | 2/1994 | Sideris |
| 5,289,817 A | 3/1994 | Williams et al. |
| 5,300,065 A | 4/1994 | Anderson |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,336,222 A | 8/1994 | Durgin, Jr. et al. |
| 5,336,227 A | 8/1994 | Nakao et al. |
| 5,337,732 A | 8/1994 | Grundfest et al. |
| 5,337,733 A | 8/1994 | Bauerfeind et al. |
| 5,342,376 A | 8/1994 | Ruff |
| 5,345,949 A | 9/1994 | Shlain |
| 5,348,259 A | 9/1994 | Blanco et al. |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst et al. |
| 5,417,699 A | 5/1995 | Klein et al. |
| 5,425,744 A | 6/1995 | Fagan et al. |
| 5,429,583 A | 7/1995 | Paulus et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,266 A | 8/1995 | McPherson et al. |
| 5,437,680 A | 8/1995 | Yoon |
| 5,437,681 A | 8/1995 | Meade et al. |
| 5,445,167 A | 8/1995 | Yoon et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,535,759 A | 7/1996 | Wilk |
| 5,540,704 A | 7/1996 | Gordon et al. |
| 5,549,621 A | 8/1996 | Bessler et al. |
| 5,558,665 A | 9/1996 | Kieturakis |
| 5,562,684 A | 10/1996 | Kammerer |
| 5,562,686 A | 10/1996 | Sauer et al. |
| 5,562,688 A | 10/1996 | Riza |

| | | | | | |
|---|---|---|---|---|---|
| 5,569,274 A | 10/1996 | Rapacki et al. | 5,840,078 A | 11/1998 | Yerys |
| 5,569,306 A | 10/1996 | Thal | 5,843,084 A | 12/1998 | Hart et al. |
| 5,571,116 A | 11/1996 | Bolanos et al. | 5,843,126 A | 12/1998 | Jameel |
| 5,571,119 A | 11/1996 | Atala | 5,846,261 A | 12/1998 | Kotula et al. |
| 5,573,496 A | 11/1996 | McPherson et al. | 5,855,614 A | 1/1999 | Stevens et al. |
| 5,573,540 A | 11/1996 | Yoon | 5,860,991 A | 1/1999 | Klein et al. |
| 5,573,548 A | 11/1996 | Nazre et al. | 5,861,003 A | 1/1999 | Latson et al. |
| 5,578,045 A | 11/1996 | Das | 5,865,791 A | 2/1999 | Whayne et al. |
| 5,582,616 A | 12/1996 | Bolduc et al. | 5,868,762 A | 2/1999 | Cragg et al. |
| 5,584,835 A | 12/1996 | Greenfield | 5,879,371 A | 3/1999 | Gardiner et al. |
| 5,584,859 A | 12/1996 | Brotz | 5,887,594 A | 3/1999 | LoCiero, III |
| 5,601,557 A | 2/1997 | Hayhurst | 5,888,247 A | 3/1999 | Benetti |
| 5,603,718 A | 2/1997 | Xu | 5,891,168 A | 4/1999 | Thal |
| 5,613,974 A | 3/1997 | Andreas et al. | 5,893,856 A | 4/1999 | Jacob et al. |
| 5,613,975 A | 3/1997 | Christy | 5,895,404 A | 4/1999 | Ruiz |
| 5,624,381 A | 4/1997 | Kieturakis | 5,897,417 A | 4/1999 | Grey |
| 5,626,588 A | 5/1997 | Sauer et al. | 5,897,562 A | 4/1999 | Bolanos et al. |
| 5,626,614 A | 5/1997 | Hart | 5,899,920 A | 5/1999 | DeSatnick et al. |
| 5,630,540 A | 5/1997 | Blewett | 5,899,921 A | 5/1999 | Caspari et al. |
| 5,632,752 A | 5/1997 | Buelna | 5,901,895 A | 5/1999 | Heaton et al. |
| 5,643,274 A | 7/1997 | Sander et al. | 5,902,254 A | 5/1999 | Magram |
| 5,643,295 A | 7/1997 | Yoon | 5,916,147 A | 6/1999 | Boury |
| 5,643,317 A | 7/1997 | Pavcnik et al. | 5,916,224 A | 6/1999 | Esplin |
| 5,643,320 A | 7/1997 | Lower et al. | 5,921,915 A | 7/1999 | Azonian et al. |
| 5,651,788 A * | 7/1997 | Fleischer et al. ............... 606/46 | 5,925,059 A | 7/1999 | Palermo et al. |
| 5,658,312 A | 8/1997 | Green et al. | 5,928,264 A | 7/1999 | Sugarbaker et al. |
| 5,658,313 A | 8/1997 | Thal | 5,944,738 A | 8/1999 | Amplatz et al. |
| 5,662,587 A | 9/1997 | Grundfest et al. | 5,947,983 A | 9/1999 | Solar et al. |
| 5,662,662 A | 9/1997 | Bishop et al. | 5,947,997 A | 9/1999 | Pavcnik et al. |
| 5,662,663 A | 9/1997 | Shallman | 5,948,001 A | 9/1999 | Larsen |
| 5,665,109 A | 9/1997 | Yoon | 5,954,732 A | 9/1999 | Hart et al. |
| 5,665,112 A | 9/1997 | Thal | 5,961,440 A | 10/1999 | Schweich, Jr. et al. |
| 5,667,513 A | 9/1997 | Torrie et al. | 5,964,765 A | 10/1999 | Fenton, Jr. et al. |
| 5,676,674 A | 10/1997 | Bolanos et al. | 5,964,782 A | 10/1999 | Lafontaine et al. |
| 5,679,005 A | 10/1997 | Einstein | 5,964,783 A | 10/1999 | Grafton et al. |
| 5,683,417 A | 11/1997 | Cooper | 5,976,073 A | 11/1999 | Ouchi |
| 5,683,419 A | 11/1997 | Thal | 5,976,127 A | 11/1999 | Lax |
| 5,690,655 A | 11/1997 | Hart et al. | 5,976,158 A | 11/1999 | Adams et al. |
| 5,693,060 A | 12/1997 | Martin | 5,976,159 A | 11/1999 | Bolduc et al. |
| 5,700,273 A | 12/1997 | Buelna et al. | 5,980,558 A | 11/1999 | Wiley |
| 5,702,421 A | 12/1997 | Schneidt | 5,984,933 A | 11/1999 | Yoon |
| 5,707,394 A | 1/1998 | Miller et al. | 5,993,476 A | 11/1999 | Groiso |
| 5,709,708 A | 1/1998 | Thal | 6,013,083 A | 1/2000 | Bennett |
| 5,713,903 A | 2/1998 | Sander et al. | 6,027,523 A | 2/2000 | Schmieding |
| 5,720,765 A | 2/1998 | Thal | 6,033,430 A | 3/2000 | Bonutti |
| 5,724,978 A | 3/1998 | Tenhoff | 6,042,155 A | 3/2000 | Lockwood |
| 5,725,552 A | 3/1998 | Kotula et al. | 6,045,497 A | 4/2000 | Schweich, Jr. et al. |
| 5,732,707 A | 3/1998 | Widder et al. | 6,045,573 A | 4/2000 | Wenstrom, Jr. et al. |
| 5,741,297 A | 4/1998 | Simon | 6,050,936 A | 4/2000 | Schweich, Jr. et al. |
| 5,749,828 A | 5/1998 | Solomon et al. | 6,053,935 A | 4/2000 | Brenneman et al. |
| 5,749,893 A | 5/1998 | Vidal et al. | 6,059,715 A | 5/2000 | Schweich, Jr. et al. |
| 5,752,963 A | 5/1998 | Allard et al. | 6,059,719 A | 5/2000 | Yamamoto et al. |
| 5,759,151 A | 6/1998 | Sturges | 6,074,401 A | 6/2000 | Gardiner et al. |
| 5,766,189 A | 6/1998 | Matsuno | 6,077,214 A | 6/2000 | Mortier et al. |
| 5,779,719 A | 7/1998 | Klein et al. | 6,077,281 A | 6/2000 | Das |
| 5,782,859 A | 7/1998 | Nicholas et al. | 6,077,291 A | 6/2000 | Das |
| 5,782,865 A | 7/1998 | Grotz | 6,079,414 A | 6/2000 | Roth et al. |
| 5,787,897 A | 8/1998 | Kieturakis | 6,086,600 A | 7/2000 | Kortenbach |
| 5,792,152 A | 8/1998 | Klein et al. | 6,110,183 A | 8/2000 | Cope |
| 5,792,153 A | 8/1998 | Swain et al. | 6,113,609 A | 9/2000 | Adams et al. |
| 5,797,929 A | 8/1998 | Andreas et al. | 6,113,611 A | 9/2000 | Allen et al. |
| 5,797,960 A | 8/1998 | Stevens et al. | 6,119,913 A | 9/2000 | Adams et al. |
| 5,810,849 A | 9/1998 | Kontos | 6,149,658 A | 11/2000 | Gardiner et al. |
| 5,810,851 A | 9/1998 | Yoon | 6,152,935 A | 11/2000 | Kammerer et al. |
| 5,810,853 A | 9/1998 | Yoon | 6,156,046 A | 12/2000 | Passafaro et al. |
| 5,810,882 A | 9/1998 | Bolduc et al. | 6,159,146 A | 12/2000 | El Gazayerli |
| 5,814,070 A | 9/1998 | Borzone et al. | 6,162,168 A | 12/2000 | Schweich, Jr. et al. |
| 5,817,110 A | 10/1998 | Kronner | 6,165,119 A | 12/2000 | Schweich, Jr. et al. |
| 5,823,956 A | 10/1998 | Roth et al. | 6,165,120 A | 12/2000 | Schweich, Jr. et al. |
| 5,824,011 A | 10/1998 | Stone et al. | 6,167,889 B1 | 1/2001 | Benetti |
| 5,827,298 A | 10/1998 | Hart et al. | 6,171,320 B1 | 1/2001 | Monassevitch |
| 5,829,447 A | 11/1998 | Stevens et al. | 6,174,323 B1 | 1/2001 | Biggs et al. |
| 5,836,955 A | 11/1998 | Buelna et al. | 6,179,195 B1 | 1/2001 | Adams et al. |

| | | |
|---|---|---|
| 6,179,776 B1 | 1/2001 | Adams et al. |
| 6,183,411 B1 | 2/2001 | Mortier et al. |
| RE37,117 E | 3/2001 | Palermo |
| 6,197,022 B1 | 3/2001 | Baker |
| 6,214,007 B1 | 4/2001 | Anderson |
| 6,228,023 B1 | 5/2001 | Zaslavsky et al. |
| 6,231,561 B1 | 5/2001 | Frazier et al. |
| 6,245,079 B1 | 6/2001 | Nobles et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,270,515 B1 | 8/2001 | Linden et al. |
| 6,283,973 B1 | 9/2001 | Hubbard et al. |
| 6,290,674 B1 | 9/2001 | Roue et al. |
| 6,293,956 B1 | 9/2001 | Crainich et al. |
| 6,296,656 B1 | 10/2001 | Bolduc et al. |
| 6,306,159 B1 | 10/2001 | Schwartz et al. |
| 6,312,437 B1 | 11/2001 | Kortenbach |
| 6,315,789 B1 | 11/2001 | Cragg |
| 6,322,563 B1 | 11/2001 | Cummings et al. |
| 6,322,580 B1 | 11/2001 | Kanner |
| 6,332,468 B1 | 12/2001 | Benetti |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,336,940 B1 | 1/2002 | Graf et al. |
| 6,346,074 B1 | 2/2002 | Roth |
| 6,348,064 B1 | 2/2002 | Kanner |
| 6,355,052 B1 | 3/2002 | Neuss et al. |
| 6,358,197 B1 | 3/2002 | Silverman et al. |
| 6,363,938 B2 | 4/2002 | Saadat et al. |
| 6,368,339 B1 | 4/2002 | Amplatz et al. |
| 6,387,104 B1 | 5/2002 | Pugsley, Jr. et al. |
| 6,394,949 B1 | 5/2002 | Crowley et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| H2037 H | 7/2002 | Yates et al. |
| 6,423,087 B1 | 7/2002 | Sawada |
| 6,425,911 B1 | 7/2002 | Akerfeldt et al. |
| 6,447,533 B1 | 9/2002 | Adams et al. |
| 6,494,888 B1 | 12/2002 | Laufer et al. |
| 6,506,196 B1 | 1/2003 | Laufer |
| 6,533,796 B1 | 3/2003 | Sauer et al. |
| 6,537,285 B1 | 3/2003 | Hatasaka, Jr. et al. |
| 6,551,315 B2 | 4/2003 | Kortenbach et al. |
| 6,554,793 B1 | 4/2003 | Pauker et al. |
| 6,554,845 B1 | 4/2003 | Fleenor et al. |
| 6,558,400 B2 | 5/2003 | Deem et al. |
| 6,572,629 B2 | 6/2003 | Kalloo et al. |
| 6,610,056 B2 * | 8/2003 | Durgin et al. ................. 606/41 |
| 6,641,592 B1 | 11/2003 | Sauer et al. |
| 6,656,194 B1 | 12/2003 | Gannoe et al. |
| 6,663,639 B1 | 12/2003 | Laufer et al. |
| 6,695,764 B2 | 2/2004 | Silverman et al. |
| 6,716,232 B1 | 4/2004 | Vidal et al. |
| 6,719,763 B2 | 4/2004 | Chung et al. |
| 6,719,764 B1 | 4/2004 | Gellman et al. |
| 6,736,828 B1 | 5/2004 | Adams et al. |
| 6,746,460 B2 | 6/2004 | Gannoe et al. |
| 6,755,843 B2 | 6/2004 | Chung et al. |
| 6,761,685 B2 | 7/2004 | Adams et al. |
| 6,773,440 B2 | 8/2004 | Gannoe et al. |
| 6,773,441 B1 | 8/2004 | Laufer et al. |
| 6,821,285 B2 | 11/2004 | Laufer et al. |
| 6,835,199 B2 | 12/2004 | McGuckin, Jr. et al. |
| 7,431,725 B2 * | 10/2008 | Stack et al. ................. 606/151 |
| 2001/0000040 A1 | 3/2001 | Adams et al. |
| 2001/0016675 A1 | 8/2001 | Mortier et al. |
| 2001/0025171 A1 | 9/2001 | Mortier et al. |
| 2001/0049509 A1 | 12/2001 | Sekine et al. |
| 2001/0051815 A1 | 12/2001 | Esplin |
| 2001/0056282 A1 | 12/2001 | Sonnenschein et al. |
| 2002/0010490 A1 | 1/2002 | Schaller et al. |
| 2002/0013608 A1 | 1/2002 | ElAttrache et al. |
| 2002/0019649 A1 | 2/2002 | Sikora et al. |
| 2002/0022851 A1 | 2/2002 | Kalloo et al. |
| 2002/0029080 A1 | 3/2002 | Mortier et al. |
| 2002/0040226 A1 | 4/2002 | Laufer et al. |
| 2002/0055757 A1 | 5/2002 | Torre et al. |
| 2002/0058855 A1 | 5/2002 | Schweich, Jr. et al. |
| 2002/0062062 A1 | 5/2002 | Belson et al. |
| 2002/0065534 A1 | 5/2002 | Hermann et al. |
| 2002/0068849 A1 | 6/2002 | Schweich, Jr. et al. |
| 2002/0068945 A1 | 6/2002 | Sixto, Jr. et al. |
| 2002/0072761 A1 | 6/2002 | Abrams et al. |
| 2002/0077524 A1 | 6/2002 | Schweich, Jr. et al. |
| 2002/0078967 A1 | 6/2002 | Sixto, Jr. et al. |
| 2002/0082621 A1 | 6/2002 | Schurr et al. |
| 2002/0082622 A1 | 6/2002 | Kane |
| 2002/0107530 A1 | 8/2002 | Sauer et al. |
| 2002/0120178 A1 | 8/2002 | Tartaglia et al. |
| 2002/0147385 A1 | 10/2002 | Butler et al. |
| 2002/0161281 A1 | 10/2002 | Jaffe et al. |
| 2002/0183768 A1 | 12/2002 | Deem et al. |
| 2002/0193661 A1 | 12/2002 | Belson |
| 2002/0193662 A1 | 12/2002 | Belson |
| 2002/0193816 A1 | 12/2002 | Laufer et al. |
| 2003/0009085 A1 | 1/2003 | Arai et al. |
| 2003/0045778 A1 | 3/2003 | Ohline et al. |
| 2003/0055442 A1 | 3/2003 | Laufer et al. |
| 2003/0065359 A1 | 4/2003 | Weller et al. |
| 2003/0109892 A1 | 6/2003 | Deem et al. |
| 2003/0139752 A1 | 7/2003 | Pasricha et al. |
| 2003/0158582 A1 | 8/2003 | Bonutti et al. |
| 2003/0167062 A1 | 9/2003 | Gambale et al. |
| 2003/0171651 A1 | 9/2003 | Page et al. |
| 2003/0171760 A1 | 9/2003 | Gambale |
| 2003/0181924 A1 | 9/2003 | Yamamoto et al. |
| 2003/0204205 A1 | 10/2003 | Sauer et al. |
| 2003/0208209 A1 | 11/2003 | Gambale et al. |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236505 A1 | 12/2003 | Bonadio et al. |
| 2003/0236536 A1 | 12/2003 | Grigoryants et al. |
| 2003/0236549 A1 | 12/2003 | Bonadio et al. |
| 2004/0010271 A1 | 1/2004 | Kortenbach |
| 2004/0030347 A1 | 2/2004 | Gannoe et al. |
| 2004/0034371 A1 | 2/2004 | Lehman et al. |
| 2004/0049095 A1 | 3/2004 | Goto et al. |
| 2004/0059346 A1 | 3/2004 | Adams et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0122452 A1 | 6/2004 | Deem et al. |
| 2004/0122453 A1 | 6/2004 | Deem et al. |
| 2004/0138682 A1 | 7/2004 | Onuki et al. |
| 2004/0147941 A1 | 7/2004 | Takemoto |
| 2004/0176784 A1 | 9/2004 | Okada |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0210243 A1 | 10/2004 | Gannoe |
| 2004/0215180 A1 | 10/2004 | Starkebaum et al. |
| 2004/0215216 A1 | 10/2004 | Gannoe et al. |
| 2004/0225305 A1 * | 11/2004 | Ewers et al. ................. 606/153 |
| 2004/0243152 A1 | 12/2004 | Taylor et al. |
| 2004/0249362 A1 | 12/2004 | Levine et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |

| | | | |
|---|---|---|---|
| 2006/0020276 A1 * | 1/2006 | Saadat et al. | 606/153 |

FOREIGN PATENT DOCUMENTS

| | | |
|---|---|---|
| EP | 0 497 781 B1 | 8/1992 |
| EP | 0 646 356 A2 | 4/1995 |
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| JP | 2004-180781 A | 7/2004 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 99/51283 A2 | 10/1999 |
| WO | WO 99/59664 A1 | 11/1999 |
| WO | WO 00/40159 A1 | 7/2000 |
| WO | WO 00/54653 A1 | 9/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/70096 A1 | 9/2001 |
| WO | WO 01/70097 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/39880 A2 | 5/2002 |
| WO | WO 02/060328 A1 | 8/2002 |
| WO | WO 02/064012 A2 | 8/2002 |
| WO | WO 02/069841 A2 | 9/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/049905 A2 | 6/2004 |
| WO | WO 2004/071284 A1 | 8/2004 |
| WO | WO 2004/075787 A1 | 9/2004 |
| WO | WO 2004/084702 A2 | 10/2004 |
| WO | WO 2004/084808 A2 | 10/2004 |
| WO | WO 2004/103189 A1 | 12/2004 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, Jul. 1987, pp. 772-776.

Brolin et al., "Experimental Evaluation of Techniques of Gastric Paritioning for Morbid Obesity", *Surgery, Gynecology & Obstetrics*, vol. 153, Dec. 1981, pp. 878-882.

Johnston et al. "The Magenstrasse and Mill Operation of Morbid Obesity", *Obesity Surgery* 13, 2003, pp. 10-16.

Okudaira et al., "The Healing and Tensile Strength of the Gastroplasty Staple Line," *The American Surgeon*, Oct. 1984, pp. 564-568.

Spivak, et al. "Endoluminal Surgery", Surgical Endoscopy, (1997) 11:321-325.

Surgical Dynamics Inc., The S D sorb Meniscal Stapler [brochure] (1997), 3 pages total.

Sutura, The Next Generation in Vascular Suturing Devices: SuperStitch [brochure], 2 pages total.

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.

Mason, "Development of Future of Gastroplasties for Morbid Obesity," *Arch Surg*, vol. 138 (Apr. 2003), pp. 362-366.

Suzuki et al., "Development of an Endoscopic Robotic System with Two Hands for Various Gastric Tube Surgeries," *Stud Health Technol Inform.* 2003;94:349-53 [Abstract Only].

* cited by examiner

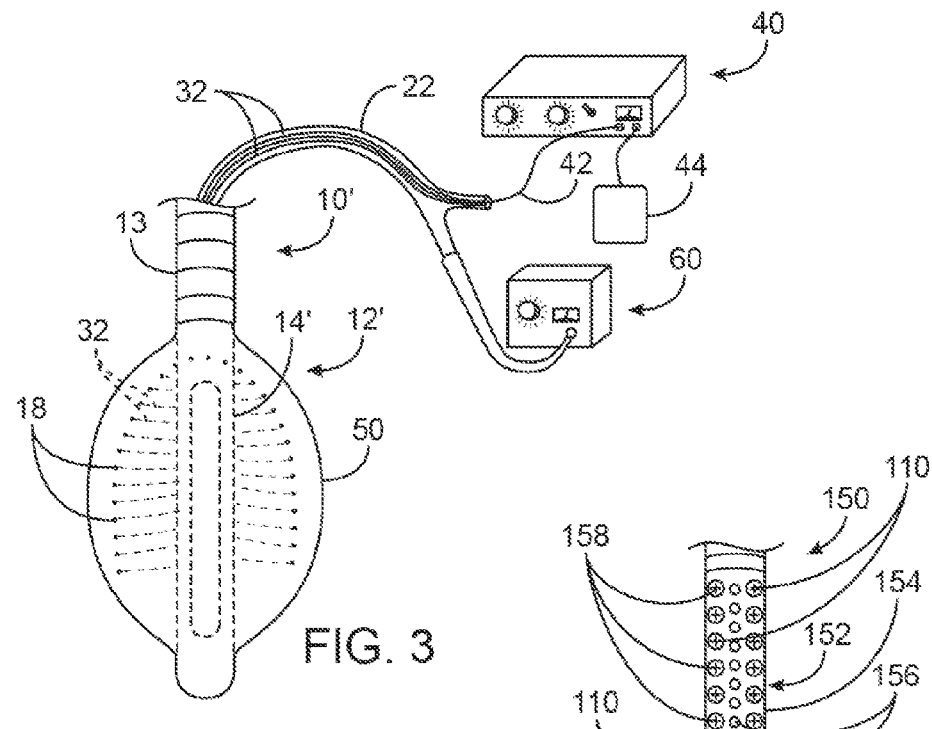
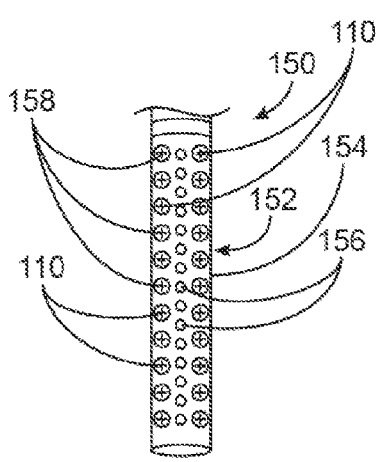
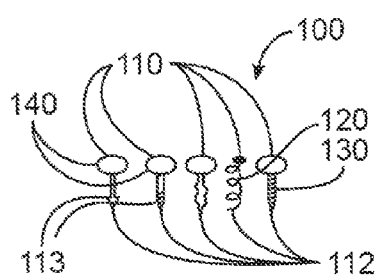
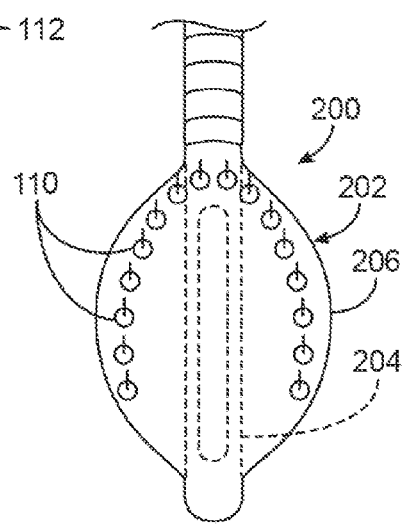

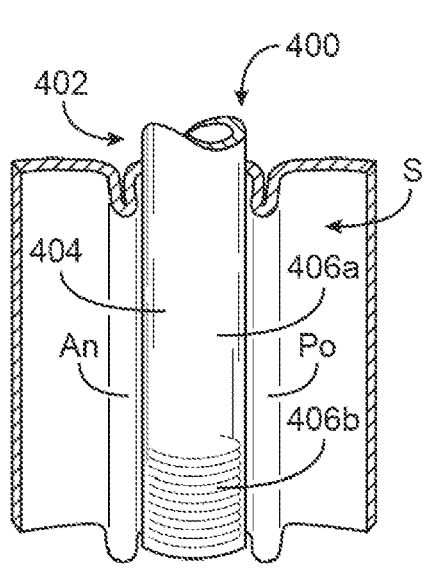
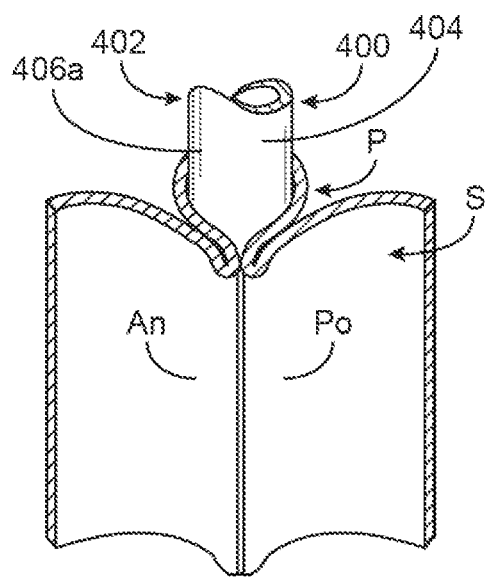
FIG. 7B    FIG. 7C
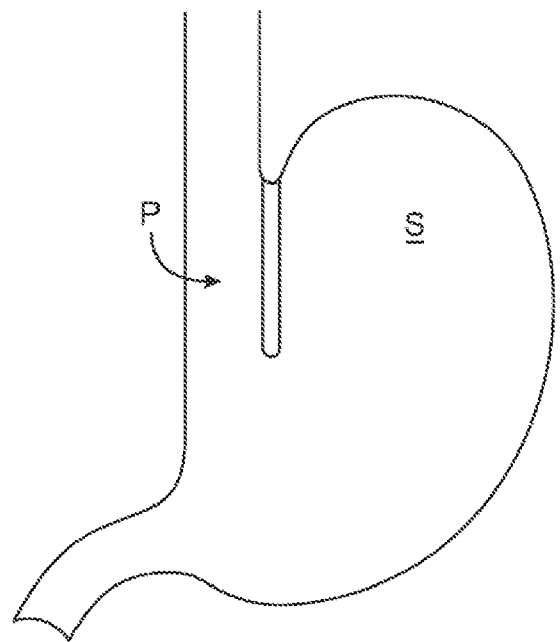
FIG. 7D

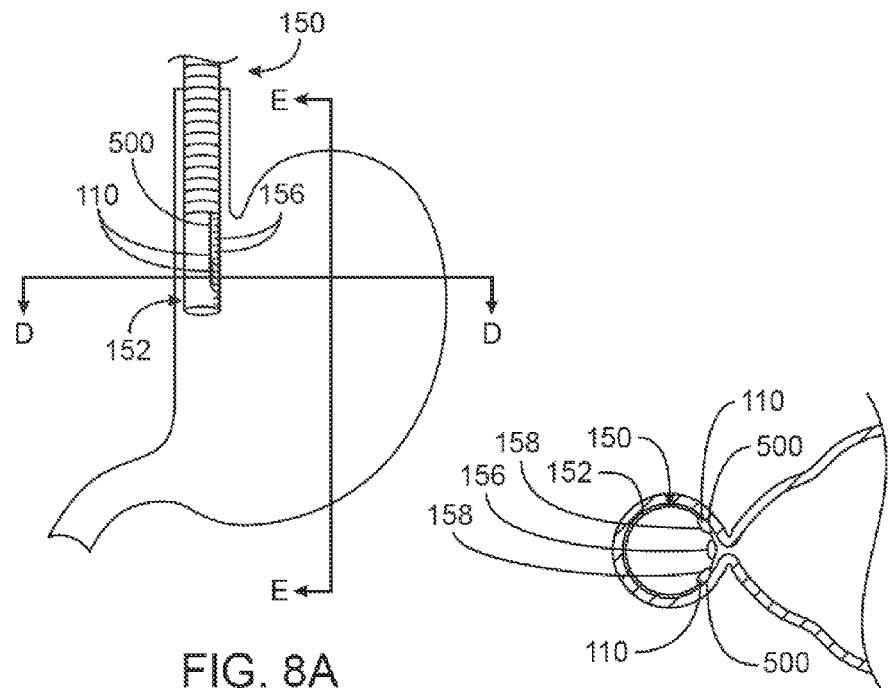
FIG. 8A
FIG. 8B
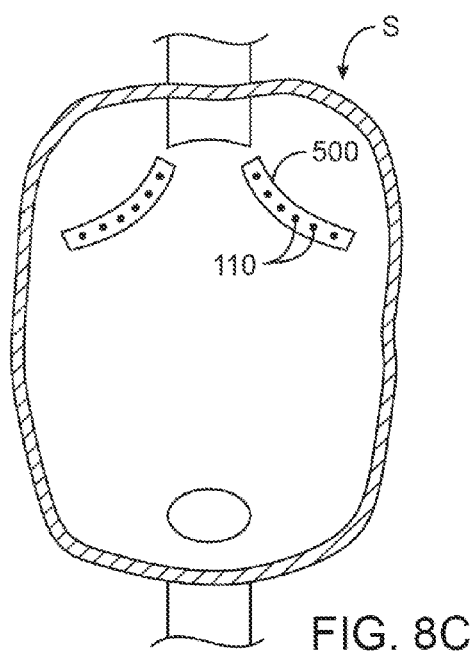
FIG. 8C

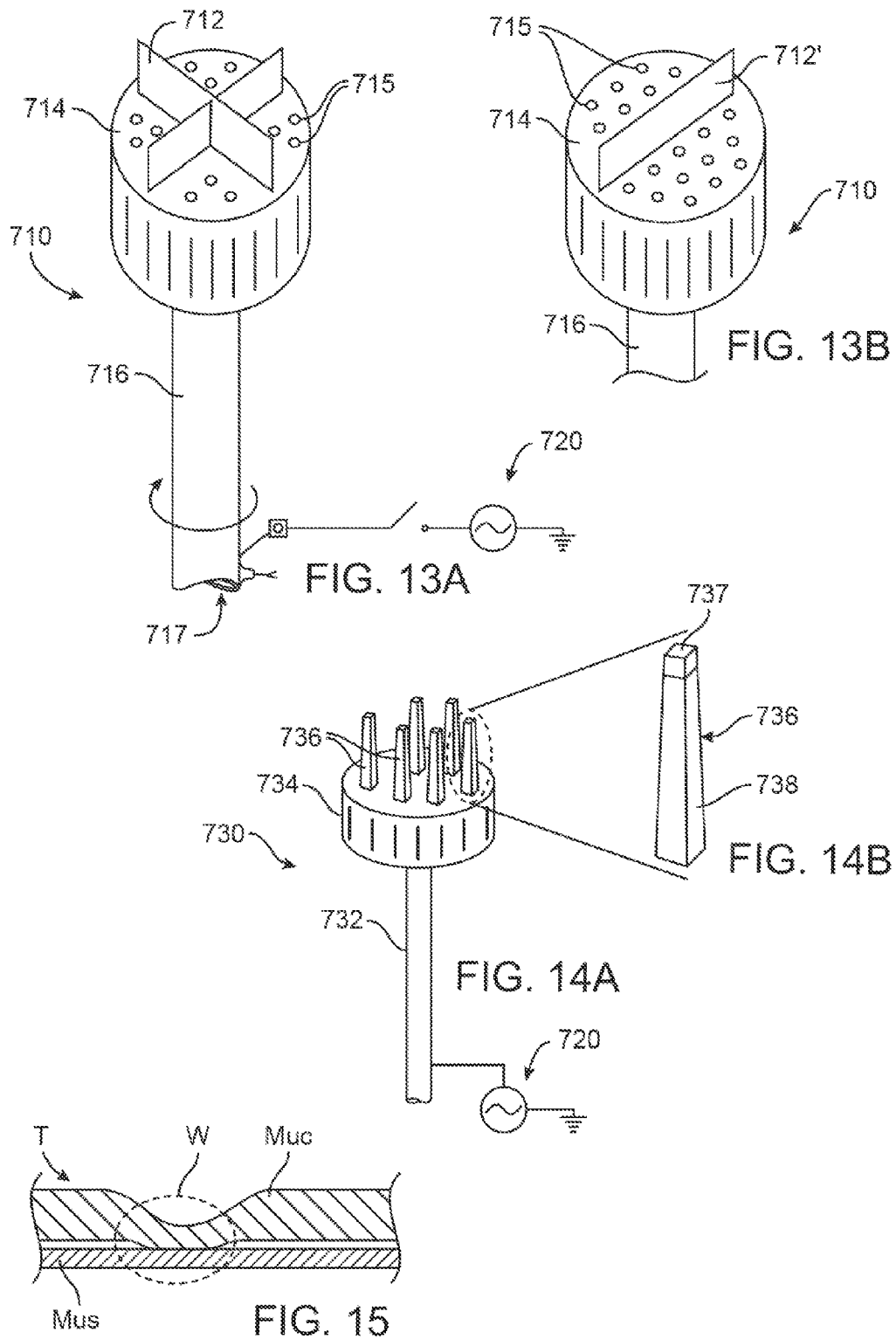

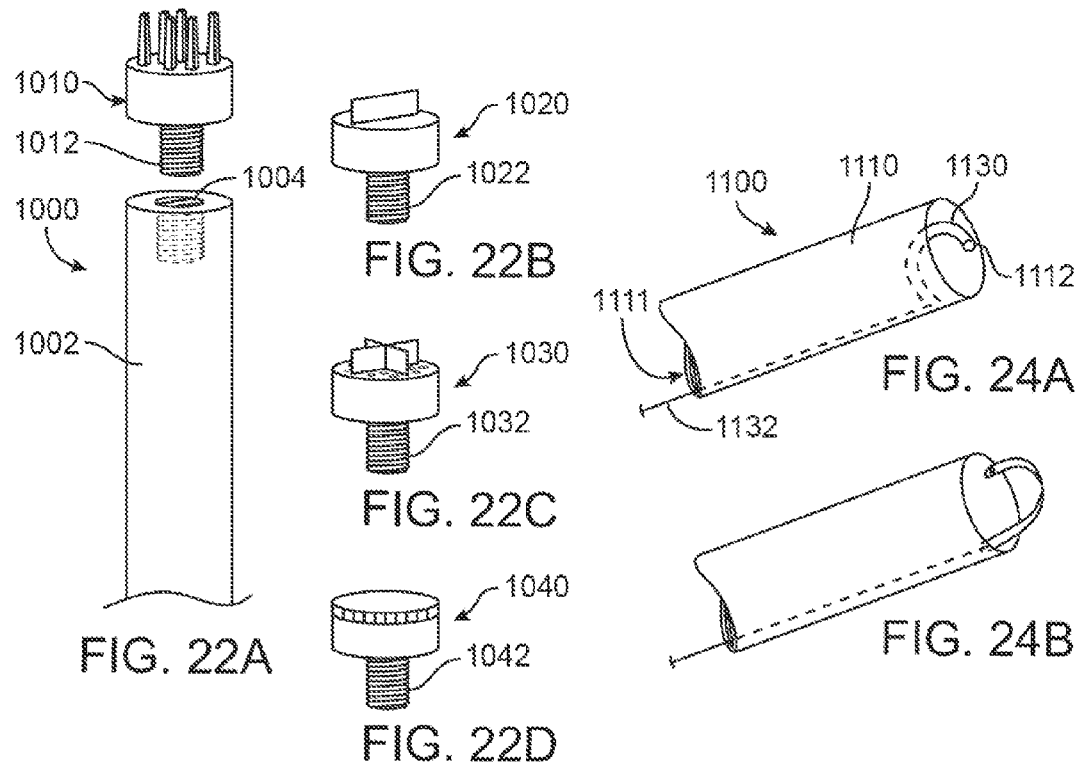
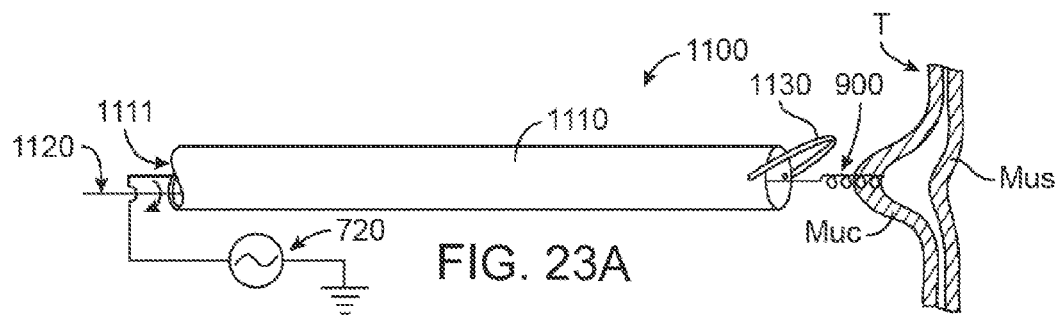
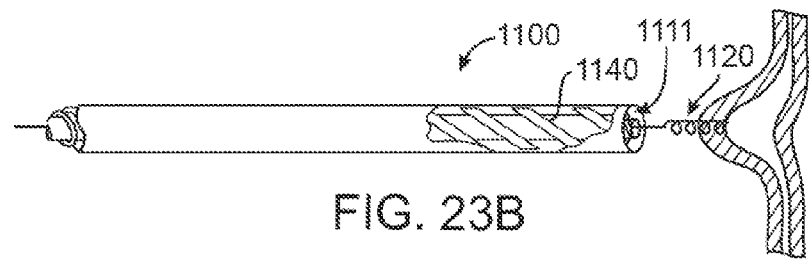

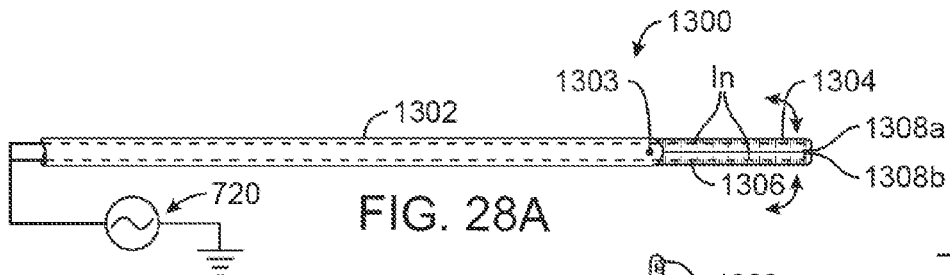
FIG. 28A
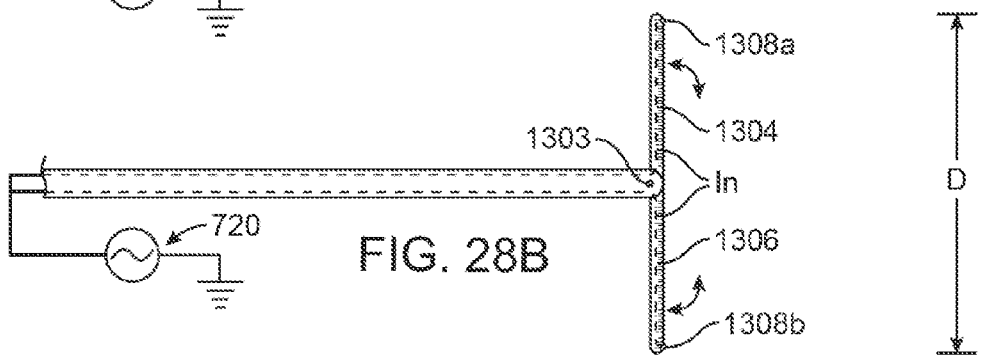
FIG. 28B
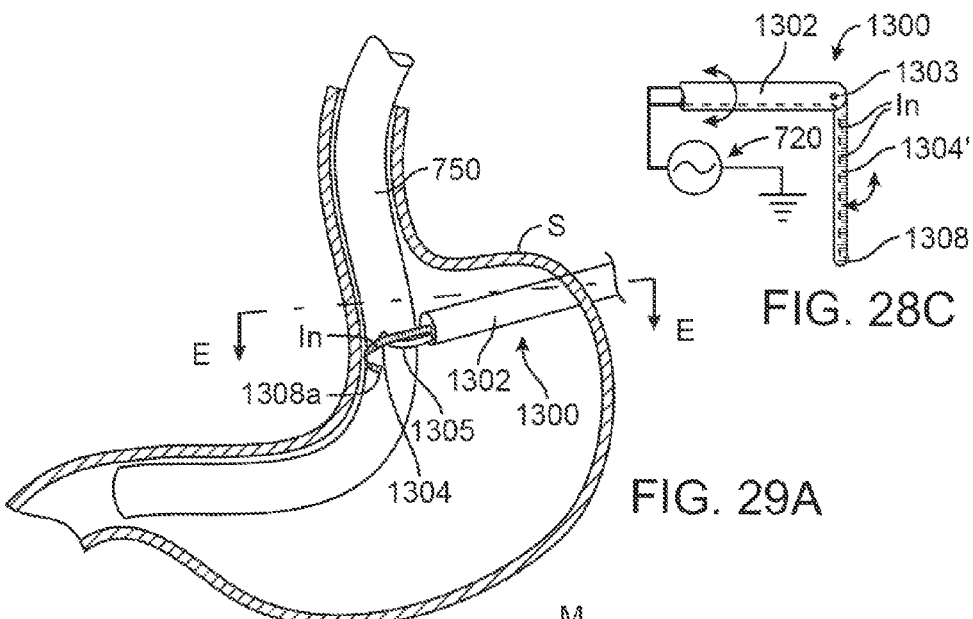
FIG. 28C
FIG. 29A
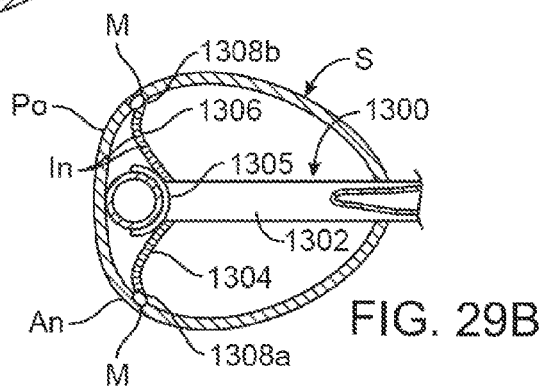
FIG. 29B

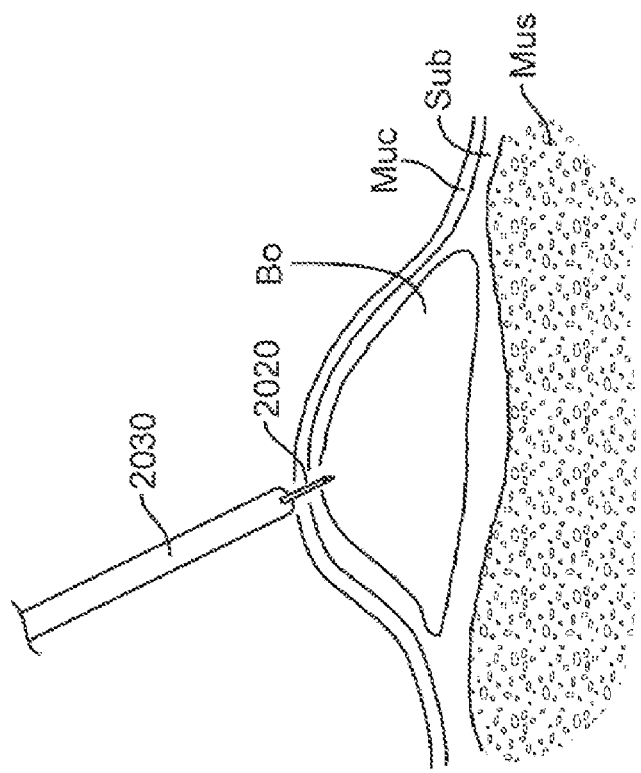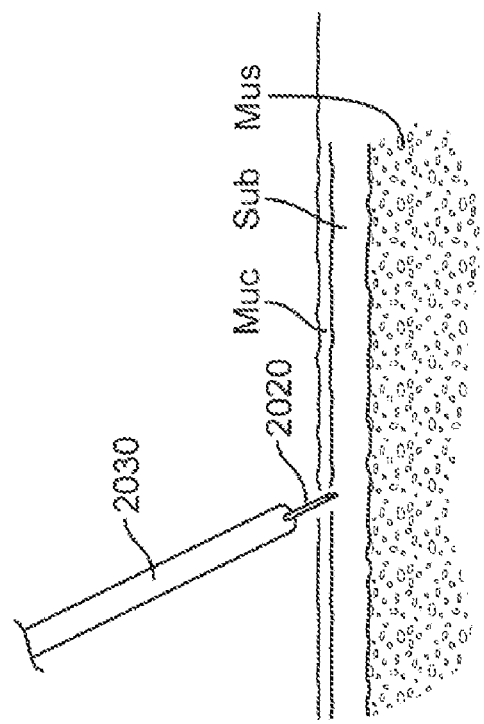
FIG. 40B
FIG. 40A

APPARATUS AND METHODS FOR MAPPING OUT ENDOLUMINAL GASTROINTESTINAL SURGERY

CROSS-REFERENCES TO RELATED APPLICATIONS

This application is a Continuation-In-Part application of co-pending U.S. patent application Ser. No. 10/797,910, filed Mar. 9, 2004, which is incorporated herein by reference in its entirety. This application also contains subject matter related to, but does not claim continuing status from, the following prior application: U.S. patent application Ser. No. 10/735,030, filed Dec. 12, 2003, which is a Continuation-In-Part of U.S. patent application Ser. No. 10/672,375, filed Sep. 23, 2003, which claims the benefit of the filing date of U.S. provisional patent application Ser. No. 60/500,627, filed Sep. 5, 2003; U.S. patent application Ser. No. 10/612,170, filed Jul. 1, 2003, and Ser. No. 10/639,162, filed Aug. 11, 2003; both of which claim the benefit of the filing date of U.S. provisional patent application Ser. No. 60/433,065, filed Dec. 11, 2002; U.S. patent application Ser. No. 10/173,203, filed Jun. 13, 2002; U.S. patent application Ser. No. 10/458,060, filed Jun. 9, 2003, which is a Continuation-In-Part of U.S. patent application Ser. No. 10/346,709, filed Jan. 15, 2003, and which claims the benefit of the filing date of U.S. provisional patent application Ser. No. 60/471,893, filed May 19, 2003; and U.S. patent application Ser. No. 10/288,619, filed Nov. 4, 2002, which is a Continuation-In-Part of U.S. patent application Ser. No. 09/746,579, filed Dec. 20, 2000, and a Continuation-In-Part of U.S. patent application Ser. No. 10/188,509, filed Jul. 3, 2002, which is a Continuation-In-Part of U.S. patent application Ser. No. 09/898,726, filed Jul. 3, 2001, which is a Continuation-In-Part of U.S. patent application Ser. No. 09/602,436, filed Jun. 23, 2000, which claims the benefit of the filing date of U.S. provisional patent application Ser. No. 60/141,077, filed Jun. 25, 1999. All of these applications are incorporated herein by reference in their entireties.

BACKGROUND OF THE INVENTION

Field of the Invention

The present invention relates to methods and apparatus for mapping out endoluminal gastrointestinal ("GI") surgery. More particularly, the present invention relates to methods and apparatus for mapping out endoluminal gastric reduction.

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several open and laparoscopic surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length. In addition, previously known open surgical procedures may present numerous life-threatening post-operative complications, and may cause atypical diarrhea, electrolytic imbalance, unpredictable weight loss and reflux of nutritious chyme proximal to the site of the anastomosis.

Applicant has previously described methods and apparatus for endoluminally reducing a patient's stomach, for example, in U.S. patent application Ser. No. 10/735,030, filed Dec. 12, 2003, which is incorporated herein by reference in its entirety. That application describes an endoluminal technique for creating a small pouch below the gastroesophageal junction to limit food intake and promote a feeling of satiety. The endoluminal pouch acts in a manner similar to a Vertical Banded Gastroplasty ("VBG").

The gastrointestinal lumen includes four tissue layers, wherein the mucosa layer is the top (innermost) tissue layer, followed by connective tissue, the muscularis layer and the serosa layer. One problem with endoluminal gastrointestinal reduction systems is that the anchors (or staples) must engage at least the muscularis tissue layer in order to provide a proper foundation, since the mucosa and connective tissue layers tend to stretch elastically under the tensile loads imposed by normal movement of the stomach wall during ingestion and processing of food. Applicant's techniques for endoluminal VBG reduction address this concern by reconfiguring the stomach lumen via engagement of at least the muscularis layer of tissue.

It is expected that proper placement of anchors or suture to achieve such endoluminal VBG will present significant challenges to a medical practitioner, due, for example, to the limited working space, as well as the limited visualization provided by, e.g., an endoscope or fiberscope. U.S. Pat. No. 6,558,400 to Deem et al. describes methods and apparatus for marking the interior of the stomach from the esophagus to the pylorus to map out an endoluminal reduction procedure. Marking is achieved with dye channeled through ports in a marking device or bougie. The bougie optionally may comprise suction ports for evacuating the stomach about the bougie, at which point the dye may be injected to stain the stomach along points that contact the dye ports. The stomach then may be insufflated for performing the endoscopic reduction procedure utilizing the map provided by the dye marks stained onto the stomach mucosa.

A significant drawback of the marking technique described by Deem et al. is that dyes have a tendency to spread and are very difficult to localize, especially in a fluid environment such as that which contacts the mucosa layer of the stomach. As such, it is expected that dye that does not penetrate beyond the mucosa will provide an inaccurate and/or unstable map for performing endoscopic gastric reduction. This, in turn, may yield an incorrectly sized or poorly sealed stomach pouch, which may render the procedure ineffective in facilitating weight loss and/or may result in dangerous complications.

In view of the aforementioned limitations, it would be desirable to provide methods and apparatus for mapping out endoluminal gastrointestinal surgery that may be readily localized.

It would be desirable to provide methods and apparatus for mapping out endoluminal gastrointestinal surgery that enhance accuracy.

It also would be desirable to provide methods and apparatus that enhance stability of the surgical map.

It would be desirable to provide methods and apparatus that facilitate direct endoluminal engagement of muscularis tissue.

It would be desirable to provide methods and apparatus that initiate a wound healing response along approximated tissue.

BRIEF SUMMARY OF THE INVENTION

In view of the foregoing, the present invention provides apparatus and methods for marking the interior of a patient's gastrointestinal lumen. In a first variation, the surgical map comprises localized RF scarring or mucosal ablation. In an alternative variation, the map comprises pegs, e.g. colored pegs, which may be biodegradable, e.g. fabricated from polyglycolic acid. Alternatively, the pegs may comprise one or more corkscrews advanced into tissue surrounding the GI lumen. In yet another alternative variation, the map comprises dye injected into at least the submucosa. The dye may be fluorescent or of varying colors. Alternatively, the dye may be disposed within nanospheres or microspheres implanted submucosally. In addition, or as an alternative, to dye spheres, the spheres may be magnetic, heat-able ferromagnetic or Curie point, plastic and inert, radiopaque, etc. As a still further alternative, the map may comprise the shaft of an endoluminal surgical tool having specified dimensions and/or color-coding, etc. In another alternative variation, the map may be formed from surgical mesh. Additional mapping apparatus will be apparent.

In one preferred variation, placement of the map is accurately achieved using suction ports and/or an inflatable member disposed along an endoluminal support, such as a shaft or other tool associated with the endoluminal GI surgery. When using suction, the stomach may be deflated about the support prior to deployment of the surgical map. When using an inflatable member, the inflatable member may be inflated to contact tissue prior to deployment of the map. As will be apparent, a combination of suction and inflation may be used to properly orient tissue prior to mapping.

In additional variations, mucosectomy and/or mucosal ablation is performed to map out endoluminal GI surgery, to facilitate direct endoluminal engagement of underlying muscularis tissue and/or to initiate a wound healing response. Specialized apparatus may be provided to achieve desired spacing and/or positioning of tissue markings, and may be provided to actually form the markings.

Methods of using apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 3 is a schematic view of an alternative variation of the apparatus of FIG. 1 that is configured to engage tissue via an inflatable member;

FIGS. 4A-4C are schematic views of alternative apparatus for mapping out an endoluminal GI surgery with pegs;

FIGS. 7A-7D are, respectively, a side view, partially in section; side-sectional detail views along section line C-C in FIG. 7A; and a side-sectional view; illustrating a method of mapping out an endoluminal GI surgery with the shaft of an endoluminal surgical tool having specified characteristics;

FIGS. 8A-8C are, respectively, a side view, partially in section; a cross-sectional detail view along section line D-D in FIG. 8A; and a side-sectional view along section line E-E in FIG. 8A, illustrating a method of mapping out endoluminal GI surgery with surgical mesh;

FIGS. 13A and 13B are schematic views of variations of the apparatus of FIG. 11 comprising irrigation;

FIGS. 14A and 14B are schematic and schematic detail views of multi-point tissue marking apparatus configured to ablate and/or weld tissue;

FIG. 15 is schematic side-sectional view illustrating a method of using the apparatus of FIG. 14 to mark and weld tissue;

FIGS. 22A-22D are schematic views of apparatus comprising removable and/or interchangeable/exchangeable heads for performing medical procedures;

FIGS. 23A and 23B are schematic side and side cut-away views, respectively, illustrating methods of using mucosectomy apparatus comprising an actuable cutting wire to remove mucosal tissue;

FIGS. 24A and 24B are schematic views of a suction engagement variation of the apparatus of FIG. 23;

FIGS. 28-28C are schematic views illustrating variations of measuring apparatus configured for mapping out endoluminal GI surgery;

FIGS. 29A and 29B are, respectively, a schematic side view, partially in section, and a cross-sectional view along section line E-E of FIG. 29A, illustrating a laparoscopic endoluminal method of using another variation of the apparatus of FIG. 28 to map out endoluminal GI surgery;

FIGS. 40A and 40B are side views, partially in section, illustrating a method of utilizing the apparatus of FIG. 39 to separate mucosal tissue from underlying muscularis tissue.

DETAILED DESCRIPTION OF THE INVENTION

The present invention relates to methods and apparatus for mapping out endoluminal gastrointestinal ("GI") surgery. More particularly, the present invention relates to methods and apparatus for mapping out endoluminal gastric reduction.

Applicant has previously described methods and apparatus for endoluminally forming and securing GI tissue folds, for example, in U.S. patent application Ser. No. 10/735,030, filed Dec. 12, 2003, which has been incorporated herein by reference. Such methods and apparatus may be used to reduce or partition the effective cross-sectional area of a GI lumen, e.g., to treat obesity by approximating the walls of the stomach to narrow the stomach lumen and/or create a pouch or endoluminal Vertical Banded Gastroplasty ("VBG"), thus promoting a feeling of satiety and reducing the area for food absorption. However, as discussed previously, it is expected that proper placement of anchors or suture to form and secure such endoluminal VBG will present significant challenges to a medical practitioner, due, for example, to the limited working space, as well as the limited visualization provided by, e.g., an endoscope or fiberscope.

Figure 1:
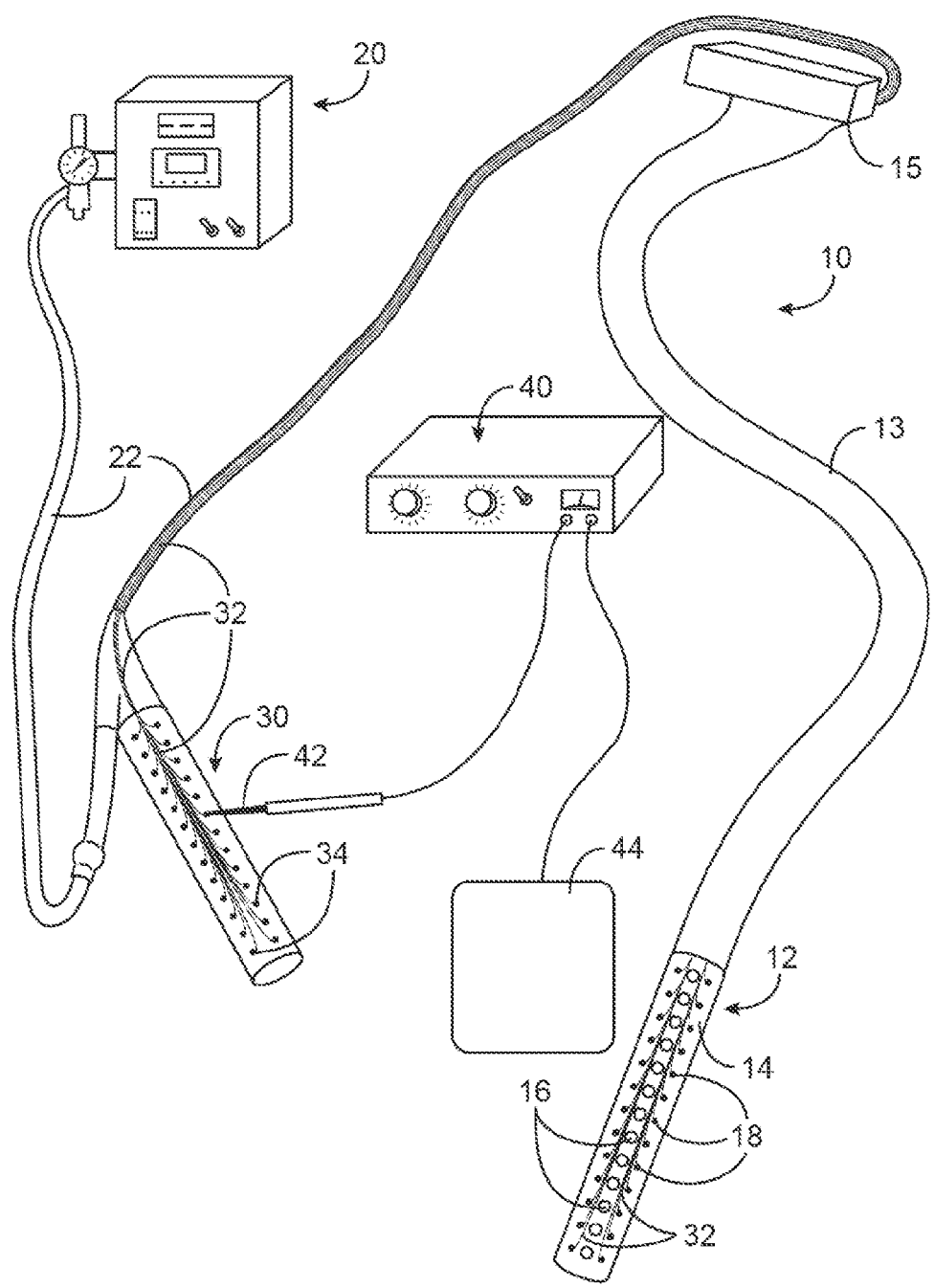
FIG. 1 is an isometric view of a first variation of apparatus of the present invention configured to map out an endoluminal gastrointestinal surgery, the apparatus comprising suction ports and RF elements configured to selectively scar or ablate the interior wall of the GI lumen.

Referring now to FIG. 1, a first variation of apparatus for mapping out endoluminal GI surgery in accordance with the present invention is described. Apparatus 10 comprises endoluminal support 12 having shaft 14 with one or more, e.g., a plurality, of suction ports 16 and one or more, e.g., a plurality, of radiofrequency ("RF") marking electrodes 18 disposed along the length of the shaft. Suction ports 16 are proximally coupled to suction pump 20 via tubing 22. Likewise, each RF marking electrode 18 is connected to switching station 30 via a wire 32. As seen in FIG. 1, wires 32 optionally may be routed through tubing 22 over at least a portion of their length. Switching station 30 comprises electrical contacts 34 that are electrically connected to RF marking electrodes 18 via wires 32. Apparatus 10 further comprises RF generator 40, which is configured to actuate electrodes 18 via switching station 30. RF generator 40 comprises positive electrode 42 and negative or ground electrode 44. RF generator 40 may comprise a commercially available RF generator, per se known, for example, such as those distributed by Everest Medical of Maple Grove, Minn.

In use, endoluminal support 12 may be endoluminally advanced within a GI lumen, e.g., a patient's stomach. Actuation of suction pump 20 from outside the patient draws suction through tubing 22 and suction ports 16, thereby bringing luminal GI tissue into contact with shaft 14 of endoluminal support 12. Meanwhile, negative electrode 44 of RF generator 40 may be placed exterior to the patient, e.g., on the patient's chest, or on a metal operating table just under the patient's back while the patient lies on the table. As will be apparent, negative electrode 44 alternatively may be coupled to endoluminal support 12, for example, along shaft 14 at a location radially distant from RF electrodes 18. Positive electrode 42 may be selectively connected to any of the plurality of electrical contacts 34 of switching station 30, as desired, to actuate specified RF marking electrodes 18.

Actuation of electrodes 18 via RF generator 40 acts to locally burn, singe, cut, ablate, scar or otherwise injure tissue in contact with the electrodes along shaft 14 of endoluminal support 12, thereby leaving identifiable marks on the surface of the tissue that may be used to map out an endoluminal GI surgery. As will be apparent to those of skill in the art, the pattern of electrodes 18 and suction ports 16 about shaft 14 of endoluminal support 12 may be altered as desired to facilitate formation of surgical maps having varying characteristics. Likewise, the shape or orientation of shaft 14 may be altered.

Switching station 30 facilitates actuation of individual electrodes 18, as well as actuation of any combination of the individual electrodes, including simultaneous actuation of all the electrodes. Such selective actuation is dependent upon which electrical contact(s) 34 are connected to positive electrode 42 of RF generator 40 when the generator is energized. As will be apparent, switching station 30 optionally may be omitted, and wires 32 may couple RF electrodes 18 directly to RF generator 40.

Endoluminal support 12 optionally may comprise one or more working lumens (not shown) for advancing additional surgical instruments through the endoluminal support. Additionally or alternatively, endoluminal support 12 optionally may comprise proximal shaft 13 that is steerable and/or rigidizable or shape-lockable, e.g. via pull wires actuated through handle 15. Rigidizable shafts are described, for example, in Applicant's U.S. patent application Ser. No. 10/735,030, filed Dec. 12, 2003, which has been incorporated herein by reference. When utilizing a steerable, rigidizable shaft, endoluminal support 12 may be steered into proper position within a GI lumen, rigidized to maintain its position, and then actuated as described above to mark tissue and map out endoluminal GI surgery.

Figure 2A:
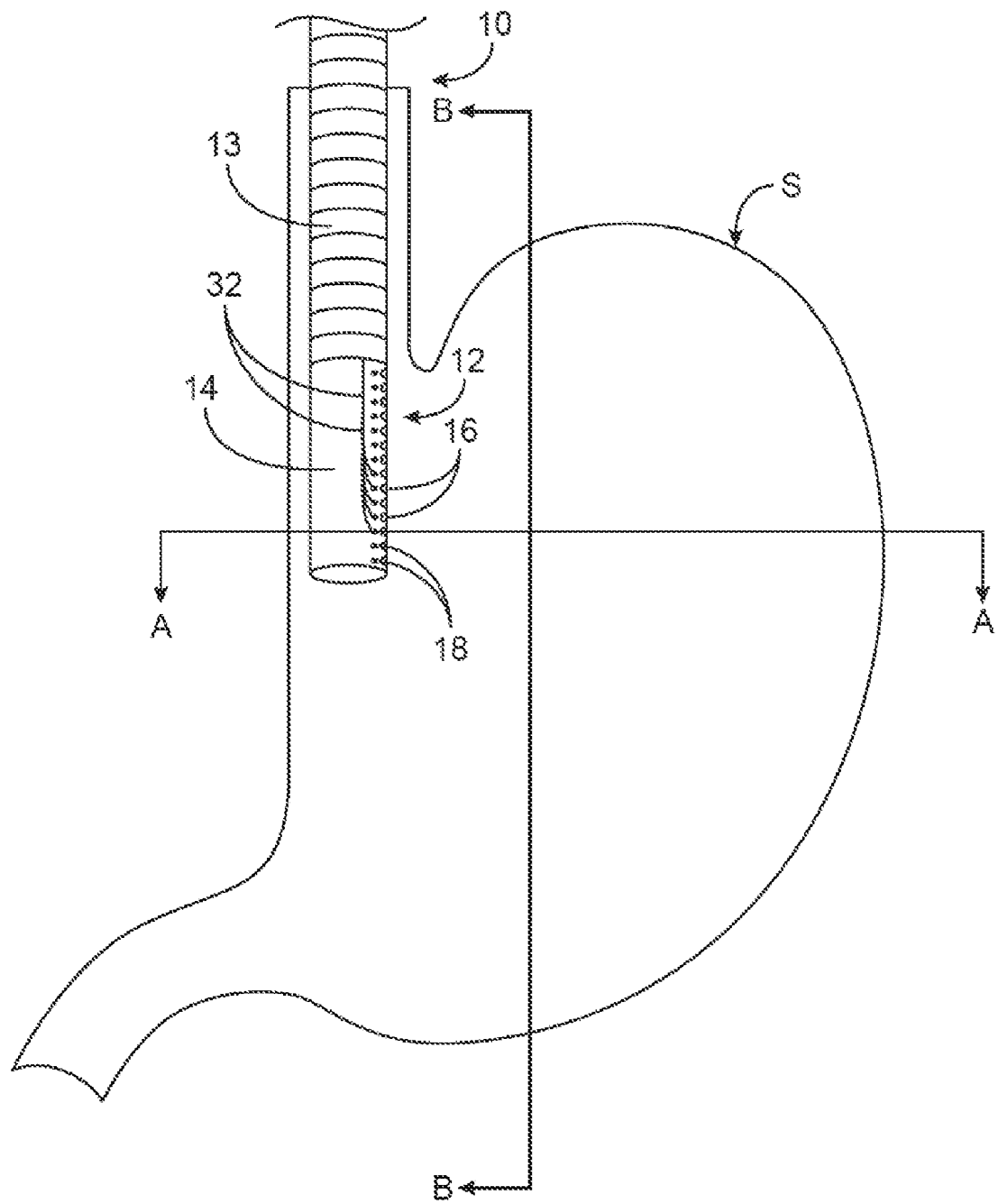
FIGS. 2A-2C are, respectively, a side view, partially in section; a cross-sectional detail view along view line A-A in FIG. 2A; and a side-sectional view along view line B-B of FIG. 2A; illustrating a method of using the apparatus of FIG. 1 to map out an endoscopic stomach reduction procedure.
Figure 2B:
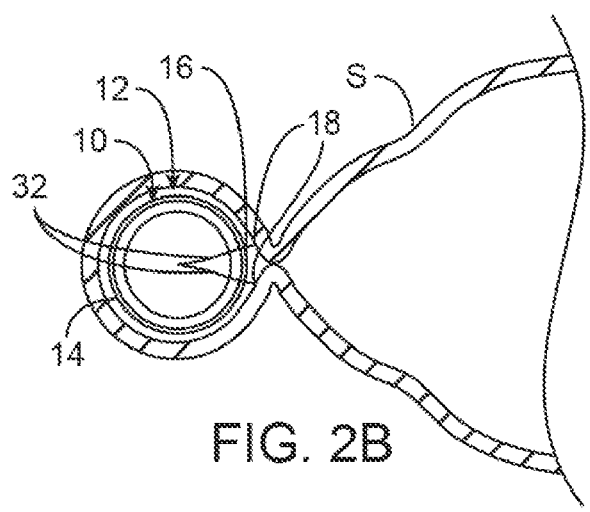

With reference now to FIG. 2, in conjunction with FIG. 1, a method of using the apparatus of FIG. 1 to map out an endoscopic stomach reduction procedure is described. In FIG. 2A, endoluminal support 12 of apparatus 10 is endoluminally advanced down a patient's throat into the patient's stomach S. Suction ports 16 and RF electrodes 18 are oriented towards the greater curvature of stomach S. Negative electrode 44 of RF generator 40 is placed exterior to the patient in close proximity to shaft 14 of apparatus 10 (not shown). Suction pump 20 is then actuated to pull suction through suction ports 16 and deflate the stomach about shaft 14 of endoluminal support 12, as in FIG. 2B. Positive electrode 42 of RF generator 40 is connected to one or more electrical contacts 34 of switching station 30, and the RF generator is actuated to locally mark the interior wall of stomach S with marks M at locations in contact with actuated electrodes 18.

Figure 2C:
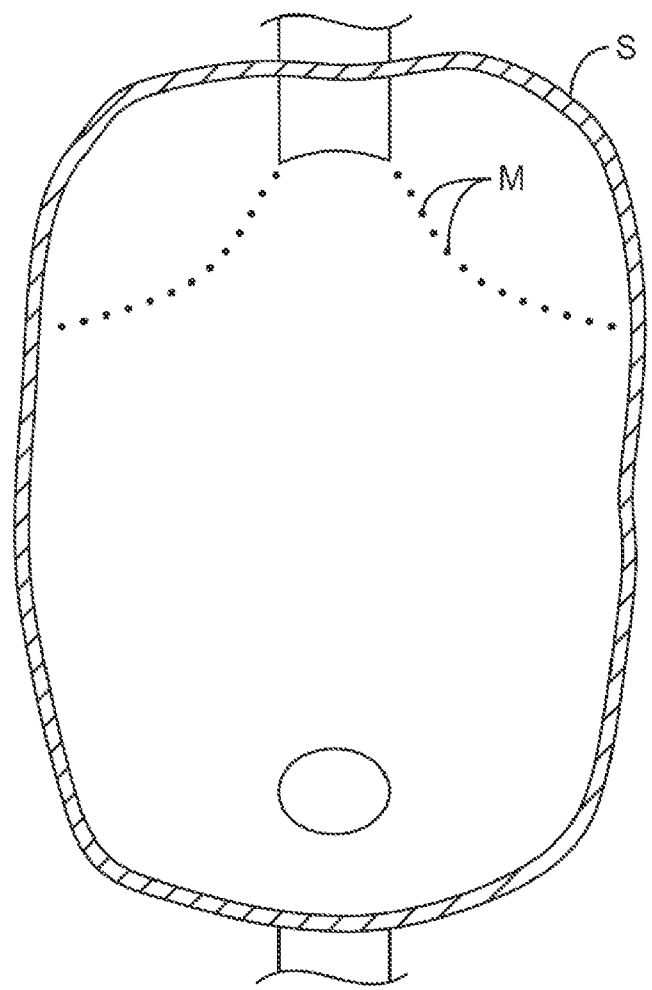

Once RF electrodes 18 have been actuated in a desired pattern and for a desired duration at a desired intensity, RF generator 40 is turned off and/or positive electrode 42 is disconnected from switching station 30. As seen in FIG. 2C, stomach S then may be insufflated, e.g., via air injected through suction ports 16. Marks M burned or ablated into the mucosa of the stomach may be used as a map for performing endoluminal stomach reduction, for example, as described in Applicant's U.S. patent application Ser. No. 10/735,030.

Referring now to FIG. 3, an alternative variation of apparatus 10 is described wherein the suction elements have been replaced with inflatable elements. Endoluminal support 12' of apparatus 10' comprises inflatable member 50 coupled to shaft 14'. Inflatable member 50 is illustratively shown at least partially inflated in FIG. 3. RF electrodes 18 are coupled to the exterior of the inflatable member in an appropriate pattern, and tubing 22 couples inflatable member 50 to inflation source 60, e.g., a compressor or a syringe. In FIG. 3, switching station 30 has been eliminated, and RF electrodes 18 have been connected directly to positive electrode 42 of RF generator 40 via wire(s) 32. In this manner, actuation of RF generator 40 energizes all electrodes 18 simultaneously.

In use, endoluminal support 12' is endoluminally advanced within a patient's stomach and/or GI lumen. Inflatable member 50 is inflated via inflation medium transferred from source 60 through tubing 22 to the inflatable member. The inflatable member conforms to the interior profile of the GI lumen, thereby bringing RF electrodes 18 into contact with the interior wall of the lumen. The electrodes then may be actuated as described previously to form marks M for mapping out an endoluminal GI surgery. As will be apparent, a combination of suction and inflation may be used to properly orient tissue prior to marking and mapping.

Referring now to FIG. 4, alternative apparatus for mapping out an endoluminal GI surgery is described. As seen in FIG. 4A, apparatus 100 comprises a plurality of pegs 110 that are configured to engage tissue and act as a map for endoluminal GI surgery. The pegs optionally may comprise sharpened distal ends 112 configured to penetrate tissue. Pegs 110 may also comprise optional barbs, hooks, etc. 113 to maintain the pegs in the tissue after penetration. The pegs may be endoluminally implanted at appropriate locations, then visualized to provide a map for the GI surgery. They preferably are colored to enhance visibility, and optionally may be provided in a variety of colors, shapes, sizes, etc. to provide additional mapping information. Pegs 110 preferably are biodegradable, e.g., fabricated from polyglycolic acid. Pegs 110 optionally may comprise a plurality of corkscrews 120. Corkscrews may require less force to advance into tissue, as compared to pegs with substantially straight shafts having sharpened distal ends 1112. The rotational motion used to advance corkscrews applies enhanced force within the plane of tissue, as opposed to perpendicular to the plane. As an alternative to corkscrews, screws 130 may be provided. Alternatively tacks 140 may be provided. Additional pegs will be apparent.

FIGS. 4B and 4C illustrate modified variations of previously described apparatus 10 and 10', respectively, that are configured to deliver and deploy pegs 110 of apparatus 100. In FIG. 4B, apparatus 150 comprises endoluminal support 152 having suction ports 156 disposed along shaft 154. Suction ports 156 are coupled to suction pump 20 via tubing 22, as described previously. Pegs 110 are disposed in channels 158 along shaft 154 and may be deployed from the channels into tissue when tissue is disposed about the shaft, e.g., via suction drawn through ports 156. Advancement of the pegs into tissue may be achieved via pushrods, e.g. torque-able pushrods (not shown). In FIG. 4B, a few pegs illustratively are shown advanced out of channels 158.

In FIG. 4C, apparatus 200 comprises endoluminal support 202 having inflatable member 206 disposed along shaft 204. Pegs 110 are lightly adhered to the surface of inflatable member 206, such that the pegs may engage tissue and decouple from the inflatable member upon inflation of the inflatable member into contact with the tissue. Various mechanisms may be provided for releasably securing pegs 110 to the surface of inflatable member 206, for example, adhesives, electromagnets, fuse mechanisms, etc.

Figure 5:
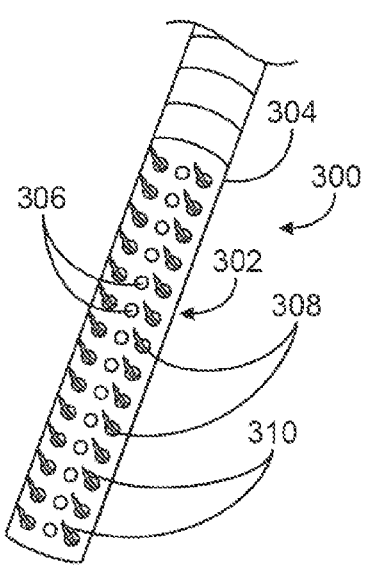
FIG. 5 is a schematic view of additional alternative apparatus for mapping out an endoluminal GI surgery, the apparatus comprising a catheter configured to locally deliver a marking element at least submucosally.

With reference now to FIG. 5, alternative apparatus for mapping out an endoluminal GI surgery is described, the apparatus comprising a marking element in combination with a catheter configured to locally deliver the marking element at least submucosally. Apparatus 300 comprises endoluminal support 302 having suction ports 306 disposed along shaft 304. Suction ports 306 are coupled to suction pump 20 via tubing 22, as described previously. Apparatus 300 further comprises injection channels 308 having retractable needles 310. Needles 310 are illustratively shown at least partially extended in FIG. 5.

In use, endoluminal support 302 may be advanced within a GI lumen with needles 310 retracted. Suction then may be drawn through ports 306 to bring tissue into proximity with channels 308. Needles 310 then may be extended into the tissue to penetrate the tissue. When conducting endoluminal gastric procedures, the needles are configured to penetrate the tissue at least submucosally. Upon penetration of tissue by needles 310, marking elements may be injected into the tissue below the surface through the needles.

Illustrative subsurface or submucosal marking elements include, but are not limited to, dyes, fluorescent dyes and colored dyes. As described in U.S. Pat. No. 6,558,400 to Deem et al., which is incorporated herein by reference, marking dyes may comprise, for example, methylene blue, thionine, acridine orange, acridine yellow, acriflavine, quinacrine and its derivatives, brilliant green, gentian violet, crystal violet, triphenyl methane, bis naphthalene, trypan blue, and trypan red. U.S. Pat. No. 6,558,400 describes using these dyes to mark or stain the interior lining of the stomach. However, that reference does not describe injecting such dyes submucosally. Submucosal injection is expected to enhance localization, stability and accuracy, as compared to mucosal staining. Additional dyes that may be utilized include black ink and India ink, as well as various combinations of dyes.

Additional subsurface/submucosal marking elements include, for example, saline or bulking agents, e.g. collagen, to achieve geometric marking/mapping via localized protrusion of the mucosa. As yet another alternative, nanospheres or microspheres may be utilized, e.g. colored spheres or dye-filled spheres. In addition, or as an alternative, to dye spheres, the spheres may be magnetic, heat-able ferromagnetic or Curie point, plastic and inert, bioresorbable, radiopaque, etc. Curie point materials may be heated to a known temperature via an external electromagnetic field, for example, to cause local ablation, inflammation or scar formation, mucosectomy, etc. Such local marking may be used to map out an endoluminal GI surgery.

Figure 6A:
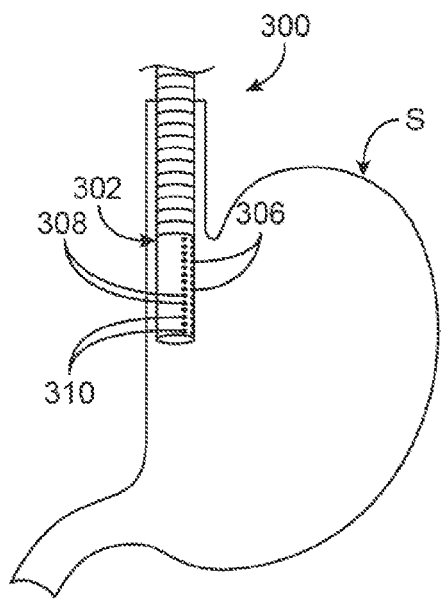
FIGS. 6A and 6B are, respectively, a side view and a side detail view, both partially in section, illustrating a method of using the apparatus of FIG. 5 to map out an endoluminal GI surgery.
Figure 6B:
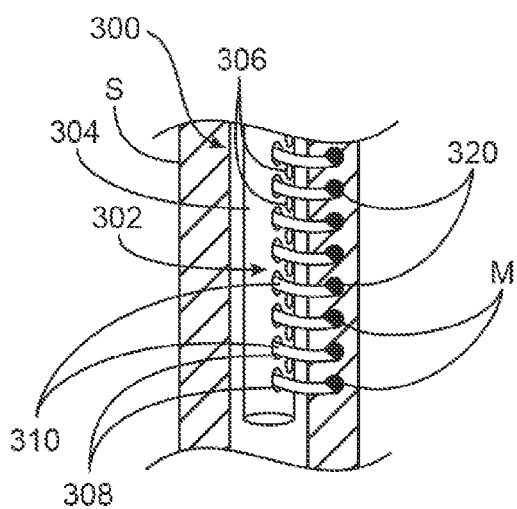

With reference now to FIG. 6, a method of using the apparatus of FIG. 5 to map out an endoluminal stomach reduction is described. In FIG. 6A, endoluminal support 302 of apparatus 300 is endoluminally advanced down a patient's throat into the patient's stomach S. Suction ports 306 and injection channels 308, having needles 310 retracted therein, are oriented towards the greater curvature of stomach S. Suction pump 20 is actuated to pull suction through suction ports 306 and deflate the stomach about shaft 304 of endoluminal support 302. Needles 310 are advanced out of injection channels 308 to penetrate tissue in proximity to the channels, as seen in FIG. 6B. The distal tips of needles 310 are disposed submucosally. Marking elements 320, which may comprise dye, spheres, etc., are injected submucosally through needles 310, thereby locally and submucosally marking the interior wall of stomach S with marks M at locations penetrated by the needles. Needles 310 are removed from the wall of stomach S, and suction pump 20 is deactivated, leaving a map of marks M within the wall of the stomach for endoluminal gastric reduction.

Referring now to FIG. 7, a method of mapping out an endoluminal gastric reduction with the shaft of an endoluminal surgical tool having specified dimensions and/or color-coding is described. Apparatus 400 comprises surgical tool 402 having shaft 404 of specified dimensions appropriate for forming an endoluminal VBG, for example, a diameter of about 1 cm. Shaft 404 optionally may also comprise a plurality of variously colored or patterned sections to provide additional mapping instructions or guideposts for a medical practitioner. In FIG. 7, shaft 404 illustratively comprises first and second sections 406a and 406b having different surface patterns.

Figure 7A:
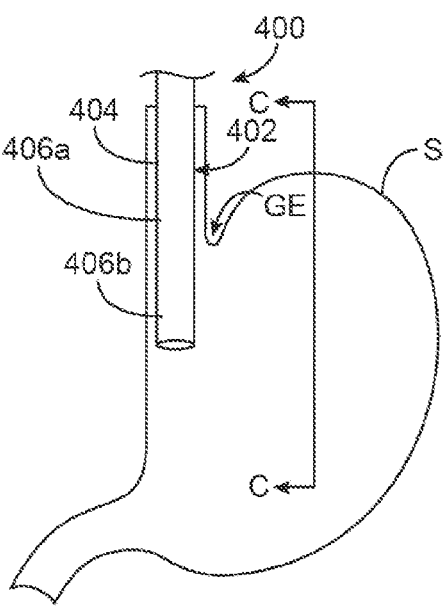

In FIG. 7A, shaft 404 is disposed in stomach S inferior to the patient's gastroesophageal junction GE. In FIG. 7B, anterior An and posterior Po tissue ridges are formed on either side of shaft 404, for example, utilizing apparatus and methods described in Applicant's U.S. patent application Ser. No. 10/735,030, which is incorporated herein by reference. The ridges are then wrapped around shaft 404 and secured to one another, as in FIG. 7C. In FIG. 7D, removal of shaft 404 leaves pouch P in stomach S, thereby completing endoluminal VBG. Apparatus 400 maps out the endoluminal VBG procedure by providing the medical practitioner with visual cues as to proper location for formation of the anterior and posterior ridges, as well as proper sizing for pouch P upon approximation of the ridges.

With reference to FIG. 8, a method of using surgical mesh to map out endoluminal GI surgery is described. In FIG. 8, apparatus 150 and pegs 110 of FIG. 4 are used in conjunction with surgical mesh strips 500, which are coupled to pegs 110 disposed in channels 158. As seen in FIG. 8A, endoluminal support 152 of apparatus 150 is advanced into a patient's stomach S. Suction is then drawn through ports 156 via pump 20, such that the stomach deflates about shaft 154 of device 152, as seen in FIG. 8B. Pegs 110 are advanced out of channels 158 into the wall of the stomach, thereby tacking surgical mesh strips 500 to the wall. As seen in FIG. 8C, suction is deactivated and apparatus 150 is removed from the patient, leaving strips 500 as a surgical map disposed on the anterior and posterior of stomach S. The strips may be used to map out the formation of ridges and a pouch in a manner similar to that described with respect to FIG. 7.

Figure 9:
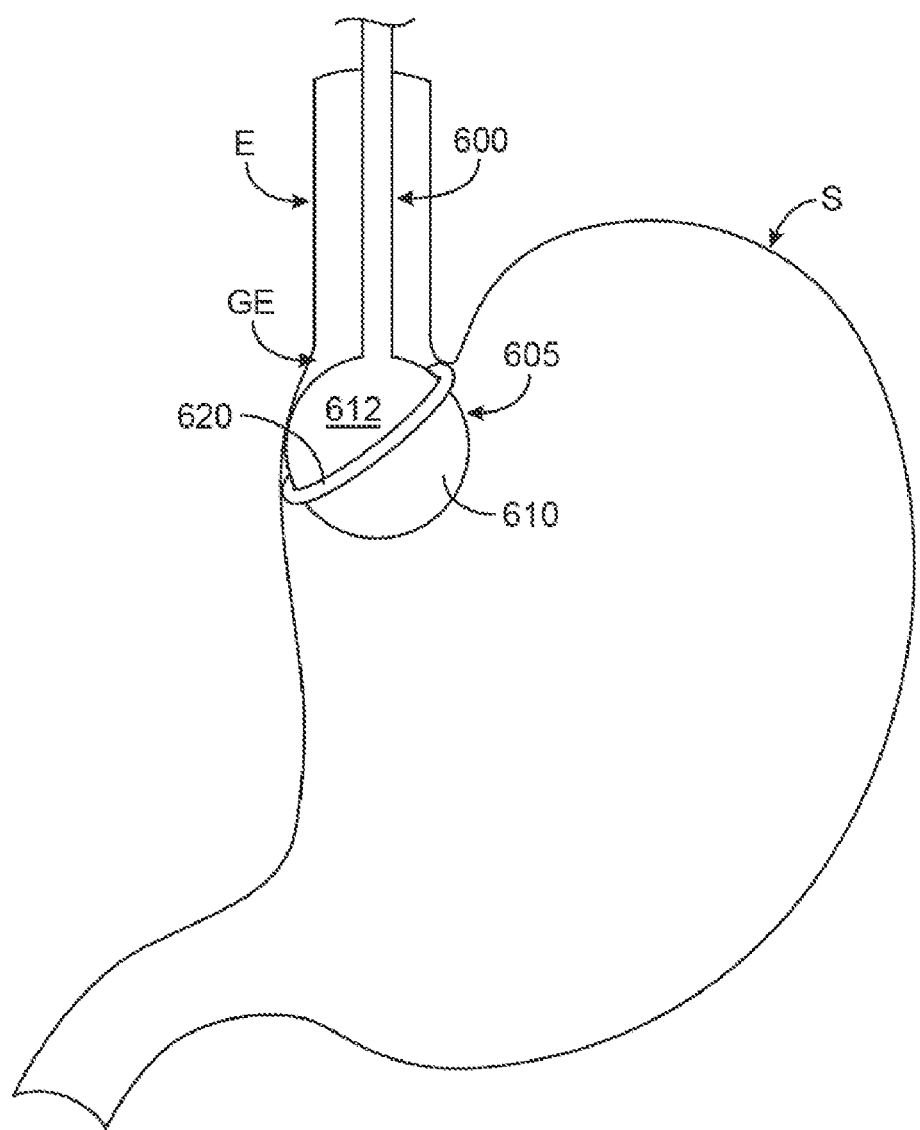
FIG. 9 is a side view, partially in section, illustrating a method of mapping out endoluminal GI surgery with an RF marking element disposed on an inflatable member.

With reference to FIG. 9, a method of mapping out endoluminal gastric reduction or restriction with an RF marking electrode disposed on an inflatable member is described. In FIG. 9, apparatus 600 comprises endoluminal support 605 having inflatable member 610 with positive RF marking electrode 620 disposed in a ring about the surface of the balloon. Ring electrode 320 preferably is flexible and 'painted' on the exterior of inflatable member 610, for example, with a conductive paint, such as a silver paint. In this manner, electrode 620 may accommodate changes in dimension as inflatable member 610 is inflated or deflated.

Inflatable member 610 is coupled to an inflation source, such as previously described inflation source 60 of FIG. 3, for inflating and deflating the member. Furthermore, RF marking electrode 620 is electrically connected to an RF generator, such as RF generator 40 of FIG. 3, which further is coupled to a negative electrode, e.g. electrode 44 of FIG. 3, that preferably is disposed external to the patient. Suction elements also may be provided, for example, suction ports 16 in communication with suction pump 20, as in FIG. 1.

In FIG. 9, endoluminal support 605 of apparatus 600 has been advanced endoluminally through esophagus E into stomach S. Inflatable member 610 then has been inflated, e.g. via inflation source 60, with a known fluid volume. Endoluminal support 605 has been retracted proximally until inflatable member 610 abuts gastroesophageal junction GE.

Ring electrode 620 then is activated, e.g. via RF generator 40, to locally singe, burn or otherwise mark the interior of stomach S. After marking, electrode 620 is deactivated, inflatable member 610 is deflated, and endoluminal support 605 of apparatus 600 is removed from stomach S, thereby leaving a map within the stomach for conducting endoluminal gastric reduction or restriction. Advantageously, the volume of fluid disposed in upper left portion 612 of inflatable member 610 (the portion of the inflatable member disposed proximal of marking electrode 620) during activation of electrode 620 substantially defines the mapped out volume of a pouch that may be formed utilizing the map provided by apparatus 600. In this manner, a stomach pouch of specified volume may be accurately formed. As will be apparent, prior to marking stomach S via activation of electrode 620, the stomach optionally may be deflated, e.g., via suction, in order to better approximate stomach tissue against inflatable member 610 and electrode 620.

Figure 10:
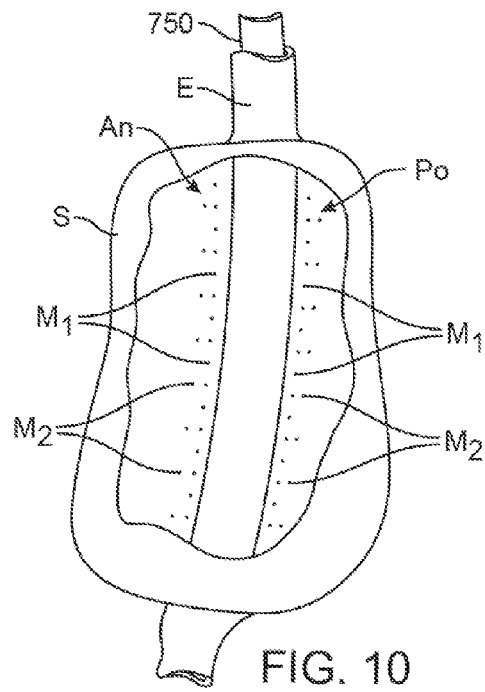
FIG. 10 is a schematic rear cut-away view, illustrating a method of mapping out endoluminal GI surgery that facilitates alignment of co-planar anterior and posterior tissue points.

Referring now to FIG. 10, a method of mapping out endoluminal GI surgery that facilitates alignment of co-planar anterior and posterior tissue points is described. As seen in FIG. 10, two rows of marks M may be formed to mark the posterior Po and anterior An positions for tissue approximation to form, e.g., a pouch within a patient's stomach S. Marks M, which may be formed utilizing any of the techniques described previously or via any other technique, illustratively comprise alternating single marks $M_1$ and double marks $M_2$. During approximation of posterior and anterior tissue to form a tissue pouch, e.g., during formation and approximation of posterior and anterior tissue folds around bougie 750 advanced through esophagus E into stomach S, marks $M_1$ and $M_2$ may provide a medical practitioner with visual indicators for proper placement of tissue anchors and/or suture. Furthermore, the alternating pattern of the marks may reduce a risk of inadvertently approximating posterior and anterior tissue segments disposed in different planes. Like properly buttoning a shirt, the marks may ensure that the right 'buttons' and 'holes' are aligned, i.e. that co-planar anterior and posterior tissue points are approximated, rather than opposing tissue points that are out of plane. Marks $M_1$ and $M_2$ may comprise any variety of shapes, e.g., circles, ellipses, etc., which are suitable for the purposes described above. Moreover, any number of marks along a single row, e.g., anterior An, may be utilized in a variety of patterns provided that the marks along the opposing row, e.g., posterior Po, are complementary so that marks $M_1$ and $M_2$ may be appropriately aligned and approximated.

Figure 11A:
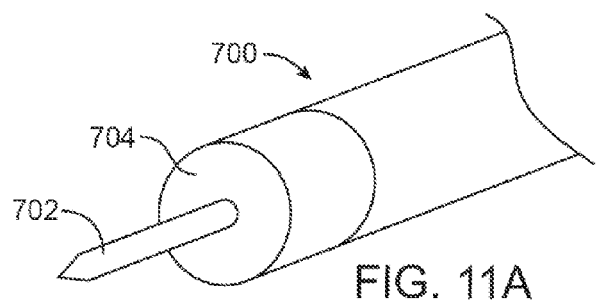
FIGS. 11A and 11B are schematic detail views of tissue marking apparatus configured to pierce and coagulate tissue.
Figure 11B:
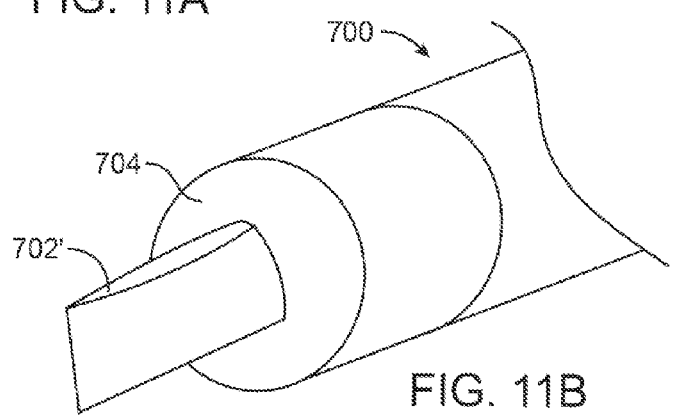

With reference to FIG. 11, variations of tissue marking apparatus configured to pierce and coagulate tissue are described. In FIG. 11A, apparatus 700 comprises piercing element 702 extending from coagulator tip 704. Both tip 704 and element 702 may be energizable, either separately or in combination, in order to locally cut, ablate, scar, burn, singe, coagulate, or otherwise injure tissue with which they come into contact. The tip and/or piercing element may, for example, be energized via RF generator 40. Optionally, tip 704 and element 702 may comprise a bipolar electrode pair. Alternatively, each may be monopolar or may individually comprise bipolar elements. FIG. 11B illustrates an alternative variation of apparatus 700 having alternative piercing element 702' that is wider that element 702 of FIG. 11A. The distal end of element 702' is sharpened to facilitate tissue piercing and may be rotated while disposed within coagulated tissue, e.g., to slough off or otherwise remove coagulated/ablated tissue.

Figure 12:
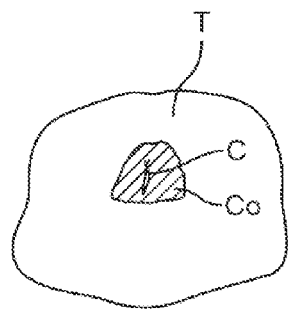
FIG. 12 is a detail schematic view illustrating a method of utilizing the apparatus of FIG. 11 to mark tissue.

Referring now to FIG. 12, a method of utilizing the apparatus of FIG. 11 to mark tissue is described. As shown, tissue T may comprise cut C formed by piercing element 702 or 702', as well as coagulated (or ablated, etc.) region Co formed with coagulator tip 704. A depth of cut C may be controlled by specifying a length of element 702/702' that extends beyond coagulator tip 704. The cut and/or the coagulated region may provide a physical marking that may be visualized for mapping out a surgical procedure. Coagulation Co is expected to reduce bleeding induced by formation of cut C and may also facilitate engagement of the coagulated tissue, as described hereinafter.

In addition to providing a physical marking, when tissue T comprises stomach tissue, cut C may locally remove mucosa and cause bleeding. If cut C is held in apposition with other tissue, the local bleeding or mucosectomy may initiate a wound healing response that gradually fuses the cut to the apposed tissue. Applicant has previously described initiation of a wound healing response to fuse tissue, for example, in U.S. patent application Ser. No. 10/898,683, filed Jul. 23, 2004, which is incorporated herein by reference in its entirety. Furthermore, local removal of the mucosa along cut C or coagulation region Co may expose underlying muscularis, which then may be engaged directly.

With reference to FIG. 13, additional variations of tissue marking apparatus configured to pierce and coagulate, as well as irrigate, tissue are described. In FIG. 13A, apparatus 710 comprises double blade piercing element 712, which optionally may be energizable, that extends from energizable coagulation tip 714 having irrigation ports 715. FIG. 13B illustrates a variation of apparatus 710 having single blade piercing element 712'.

Tip 714 is coupled to torqueable shaft 716 having irrigation lumen 717 that is connected to ports 715. Fluid irrigants may be injected through lumen 717 of shaft 716 and ports 715 of tip 714. Shaft 716 also conveys electromagnetic impulses between energy source 720 (which may, for example, comprise RF generator 40) and tip 714 or piercing element 712/712'. In use, element 712/712' may pierce tissue, tip 714 may coagulate tissue, and irrigation ports 715 may convey irrigants for cooling pierced and/or coagulated tissue. Furthermore, shaft 716 may be torqued while piercing element 712/712' is disposed within tissue; in this manner, tissue singed, burned, coagulated, etc., with tip 714 may be removed.

With reference to FIG. 14, multi-point tissue marking apparatus configured to ablate and/or weld tissue is described. As seen in FIG. 14A, apparatus 730 comprises shaft 732 coupled to energy source 720 and having tip 734 with multiple elongate elements 736. As seen in the detail view of FIG. 14B, each element 736 comprises energizable core 737 surrounded by insulated sleeve 738. Sleeve 738 extends near the distal end of each element 736, such that core 737 is only exposed for ablating or welding tissue, etc., at the distal tip of the element.

Referring to FIG. 15, a method of using apparatus 730 to mark and weld tissue is described. Mucosal tissue layer Muc and muscularis tissue layer Mus of stomach tissue T have been welded together within weld zone W. Such welding may be achieved, for example, with an elongate element 736. The exposed distal core of such an element may be placed in contact with tissue in the weld zone and energized to weld the mucosal tissue to the muscularis tissue. As apparatus 730 comprises multiple elements 736, this procedure may be repeated at several points simultaneously.

Malleable submucosal connective tissue, which weakly joins muscularis tissue to mucosal tissue; as well as the composition of mucosal tissue itself, may make it challenging to securely engage muscularis tissue from the interior of a patient's stomach. Thus, in addition to providing tissue marks that may be used to map out a surgical procedure, use of apparatus 730 may facilitate engagement of tissue within the weld zone(s). Such engagement may be achieved due to more secure binding of the mucosal layer to the muscularis layer, as well as denaturing or denuding of the mucosal layer.

Figure 16:
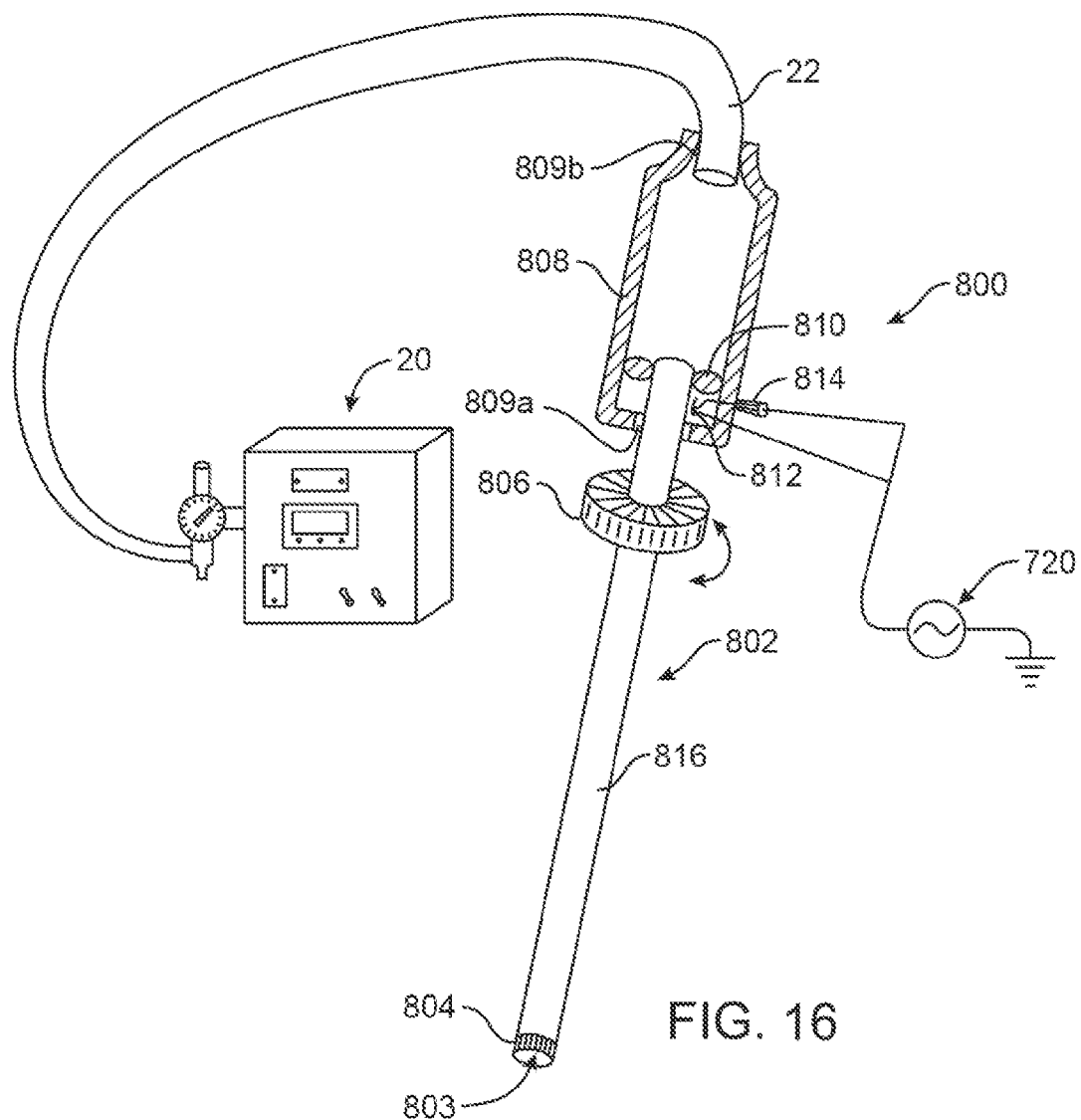
FIG. 16 is a schematic view illustrating a method of marking tissue with apparatus configured for plug mucosectomy and electrocautery.

With reference now to FIG. 16, a method of marking tissue with apparatus configured for plug mucosectomy and electrocautery is described. Apparatus 800 comprises shaft 802 having lumen 803 and sharpened distal tip 804. Shaft 802 illustratively comprises knob 806 for rotating the shaft; however, shaft 802 alternatively or additionally may be rotated via a motor (not shown). The shaft is proximally disposed within hollow handle 808 through distal port 809a. Handle 808 further comprises proximal port 809b, which is coupled to suction pump 20 via tubing 22, and O-ring 810, which may facilitate rotation of shaft 802 and which provides a seal for drawing suction through lumen 803 of the shaft.

Handle 808 also comprises floating electrical connection 812 coupled to electrical jack 814, which is connected to energy source 720, e.g., RF generator 40. Connection 812 contacts shaft 802 and facilitates energizing of the shaft during concurrent rotation thereof, e.g., via knob 806. Shaft 802 comprises insulation sleeve 816 that covers the shaft between the point of contact with electrical connection 812 and the sharpened distal tip 804. In this manner, distal tip 802 may be energized selectively via energy source 720.

As seen in FIG. 16, sharpened distal tip 804 may be advanced against tissue T, and suction may be drawn through lumen 803 of shaft 802, such that the sharpened distal tip pierces the tissue and is advanced therein. Shaft 802 may be rotated via knob 806, and tip 804 may be energized, such that plug mucosectomy PM is formed and cauterized within tissue T. Plug mucosectomy PM marks the tissue and may be used to map out a surgical procedure. Furthermore, removal of the mucosa Muc may facilitate grasping or other engagement of the underlying muscularis Mus, and also may facilitate optional initiation of a wound healing response through apposition of plug mucosectomy PM with other tissue.

Figure 17:
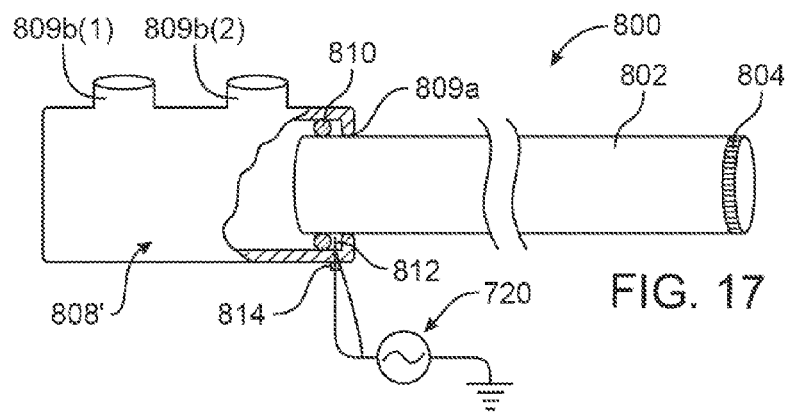
FIG. 17 is a schematic side view of a variation of the apparatus of FIG. 16 comprising irrigation.

Referring to FIG. 17, a variation of apparatus 800 is described comprising optional irrigation. In FIG. 17, handle 808' comprises ports 809b(1) and 809b(2). Port 809b(1) may, for example, be coupled to suction pump 20 via tubing 22, as described previously, while port 809b(2) may be coupled to an irrigation source for injecting fluids through lumen 803 of shaft 802. In this manner, apparatus 800 may provide for both energizing and delivery of fluids at the position of plug mucosectomy.

Figure 18:
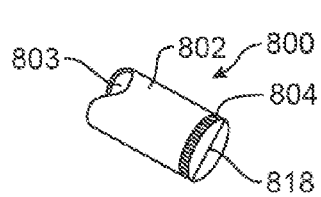
FIG. 18 is a schematic view of another variation of the apparatus of FIG. 16 comprising a cutting wire.

Referring to FIG. 18, another variation of apparatus 800 is described comprising cutting wire 818, which optionally may be energizable. Wire 818 is used in combination with distal tip 804 to form a plug mucosectomy. The wire severs the mucosal tissue layer from the muscularis tissue layer during rotation of shaft 802 for formation of the plug mucosectomy. The wire may also ablate or coagulate tissue while energized. Wire 818 optionally may be energized alone or concurrently with tip 804 (e.g., as part of a bipolar electrode pair), and optionally may be energized while suction is drawn and/or irrigants are injected through lumen 803 of shaft 802.

Figure 19A:
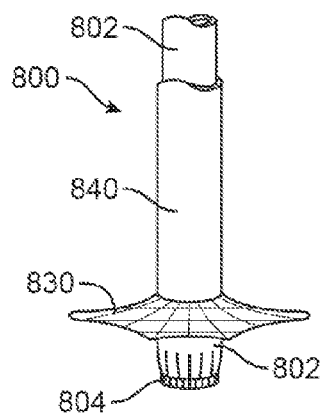
FIGS. 19A-19C are schematic views of variations of the apparatus of FIG. 18 comprising depth-limiting elements.

With reference now to FIG. 19, further variations of apparatus 800 are described comprising depth-limiting elements. The depth-limiting elements optionally may be energized and utilized in combination with tip 804 to form a bipolar electrode pair. In FIG. 19A, apparatus 800 comprises expandable mesh 830. Mesh 830 is distally coupled to shaft 802 and is proximally coupled to tube 840. Tube 840 is coaxially disposed about shaft 802 and may be advanced relative to the shaft to expand the mesh, as shown. In the expanded configuration, mesh 830 may contact tissue to limit a depth of tissue cutting. Mesh 830 also may be collapsed to a lower profile delivery and retrieval configuration by retracting tube 840 relative to shaft 802.

Figure 19B:
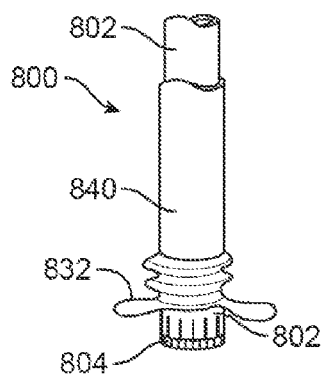
Figure 19C:
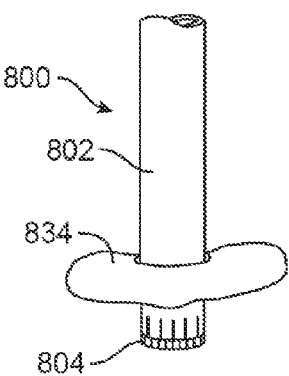

In FIG. 19B, apparatus 800 comprises expandable bellows 832 that is distally coupled to shaft 802 and proximally coupled to tube 840. As with mesh 830, bellows 832 may be expanded and collapsed via movement of tube 840 relative to shaft 802. FIG. 19C illustrates another variation of apparatus 800 comprising inflatable balloon 834 disposed near distal tip 804 of shaft 802. Balloon 834 may be inflated to contact tissue and limit a depth of tissue cutting. As with the previous variations, suction and/or irrigation may be provided in combination with FIG. 19.

Referring to FIG. 20, a method of using apparatus 800 to map out endoluminal GI surgery, as well as to directly engage muscularis tissue and to actually perform endoluminal gastric reduction or partition, is described. Apparatus 800 may be advanced, e.g., endoluminally, laparoscopically, etc., into stomach S, and a plurality of plug mucosectomies PM may be formed along opposing anterior An and posterior Po rows within the stomach, as in FIG. 20A. The opposing rows provide a medical practitioner with a map for performing an endoluminal gastric restriction procedure. For example, an anterior plug mucosectomy may be engaged for forming a tissue fold, and a co-planar posterior plug mucosectomy may be engaged to form an opposing tissue fold that may be approximated with the anterior tissue fold to form a localized partition of the stomach. This procedure may be repeated, concurrently or sequentially, until anterior and posterior tissue folds have been brought into apposition along the opposing rows of plug mucosectomies, thereby partitioning the patient's stomach, e.g., forming a pouch therein, as described hereinbelow. The map provided by plug mucosectomies PM may guide formation of the tissue folds to ensure proper placement, spacing, etc., of the folds.

Advantageously, plug mucosectomies PM may facilitate direct internal engagement of gastric muscularis tissue. In FIG. 20B, corkscrew engagement element 900 illustratively has been advanced through tissue folding and securing apparatus 910, and into a plug mucosectomy for direct internal engagement of the muscularis. It is expected that direct engagement of muscularis (e.g., engagement of muscularis without encountering intervening mucosa, or engagement through welded or ablated mucosa) will reduce a length, size and/or required working space of apparatus for internally engaging, folding and securing gastric tissue. Exemplary variations of such engaging, folding and securing apparatus, including methods of use, are described in Applicant's co-pending U.S. patent application Ser. No. 10/955,245, filed Sep. 29, 2004, (now U.S. Pat. No. 7,347,863) and entitled "Apparatus and Methods for Manipulating and Securing Tissue", which is incorporated herein by reference in its entirety FIGS. 20C-20F are detail views of element 900 and apparatus 910 illustrating direct muscularis engagement, as well as formation and approximation of opposing tissue folds. As seen in FIG. 20C, corkscrew engagement element 900 has been advanced within posterior Po plug mucosectomy PM, and has directly engaged muscularis tissue Mus. In FIG. 20D, element 900 is retracted relative to tissue folding apparatus 910, thereby drawing stomach tissue T between first bail 912 and second bail 914 of apparatus 910, and forming posterior tissue fold $F_p$. As seen in FIG. 20E, launch tube 916 of apparatus 910 may be reconfigured from a low profile delivery configuration to a deployment configuration substantially perpendicular to tissue fold $F_p$. Needle 918 they may be advanced through tube 916 and across the tissue fold. As seen in FIG. 20F, securing element 920 may be deployed through needle 918 for temporarily or permanently maintaining the tissue fold. This procedure may be repeated to form opposing anterior tissue fold $F_a$, and the anterior and posterior tissue folds may be approximated to locally partition a patient's stomach.

Figure 20A:
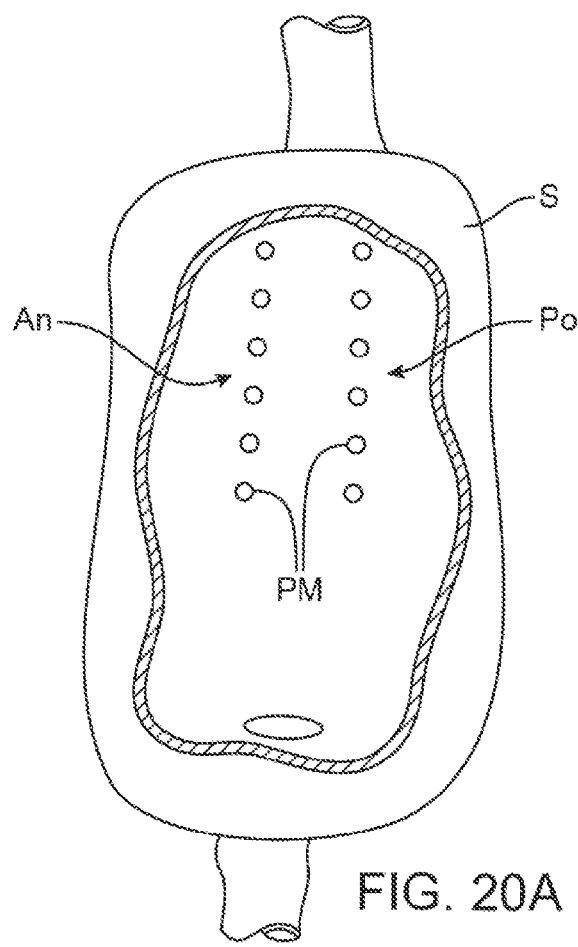
FIGS. 20A-20H are a schematic rear cut-away view, a side-sectional view, detail schematic side sectional views and a detail schematic isometric sectional view, illustrating a method of using the apparatus of FIGS. 16-19 to map out endoluminal GI surgery, to facilitate direct engagement of muscularis, and to perform endoluminal gastric reduction or partition.
Figure 20B:
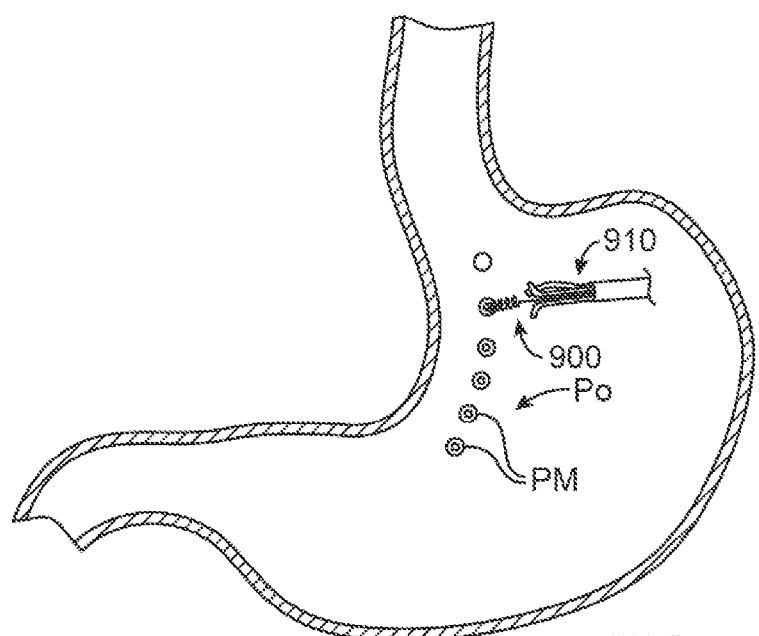
Figure 20C:
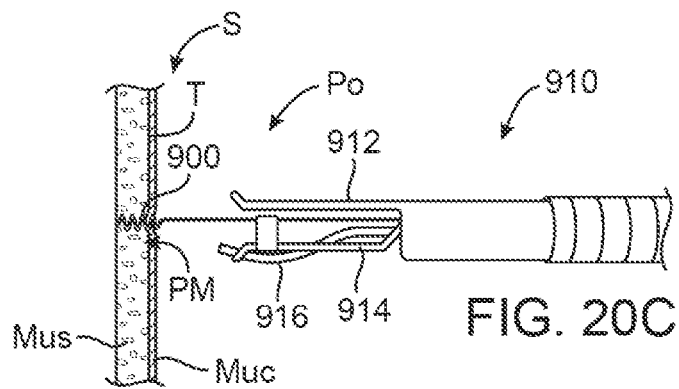
Figure 20D:
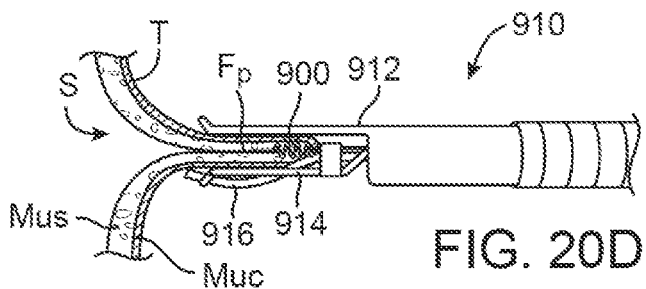
Figure 20E:
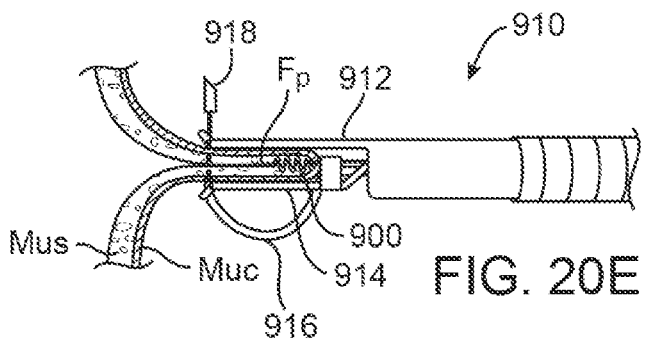
Figure 20F:
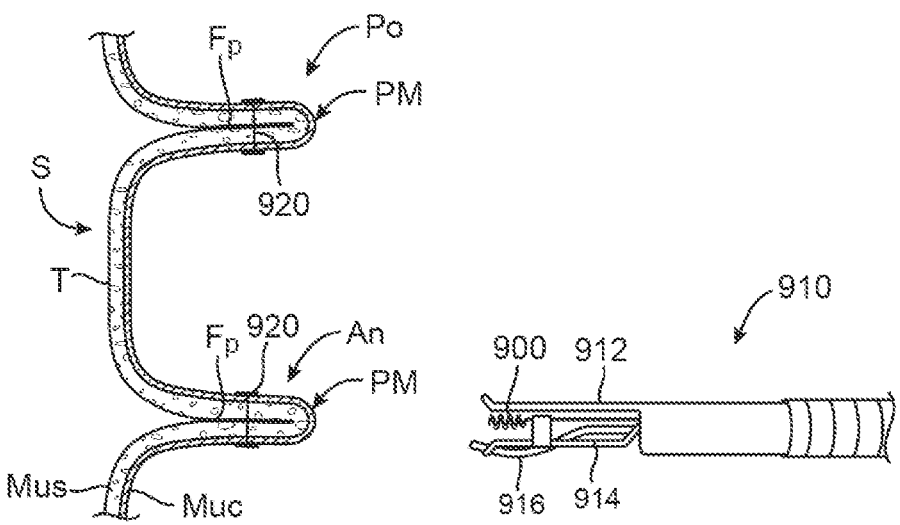
Figure 20G:
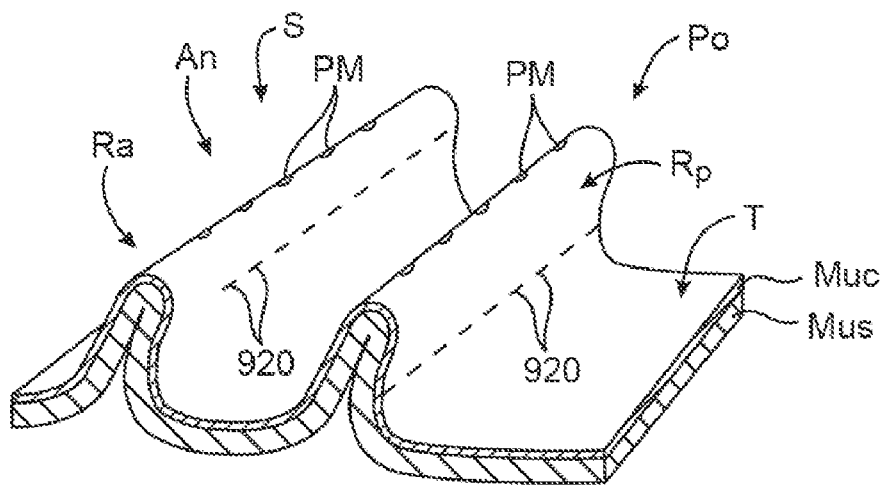
Figure 20H:
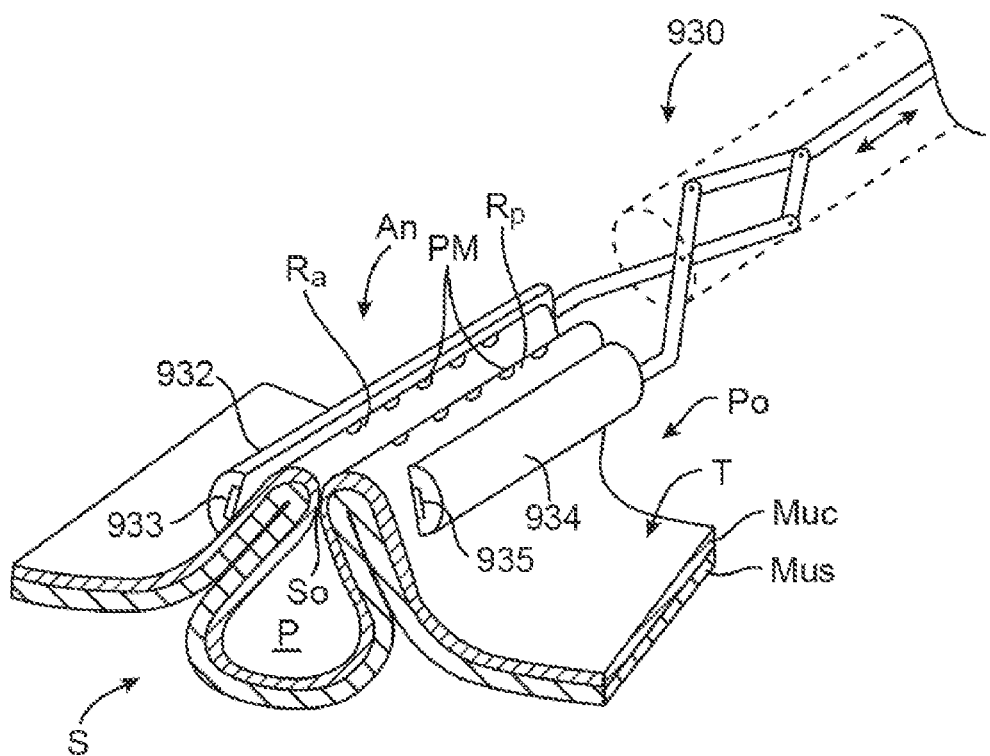

Concurrently or sequentially (or both), opposing rows of anterior $R_a$ and posterior $R_p$ tissue folds may be formed along the opposing anterior and posterior rows of plug mucosectomies PM of FIG. 20A, as seen in FIG. 20G. As seen in FIG. 20H, the opposing rows may be approximated, either during formation of individual opposing folds or after formation of opposing rows of folds (or both), to form pouch or partition P within stomach S. The rows of opposing tissue folds may be approximated and secured together in a variety of ways, e.g., via securing elements or suture. Alternatively, the rows may be clamped (temporarily or otherwise) or held against one another for welding the tissue together. Various tissue clamping devices have been described previously which have been utilized for various purposes, for example, U.S. SIR No. H2037 to Yates et al. and U.S. Pat. No. 5,300,065 to Anderson, both of which are incorporated herein by reference in their entireties, describe in further detail clamping tools that may be used for welding or sealing tissue.

As seen in FIG. 20H, illustrative bipolar clamping and welding tool 930 may be utilized to approximate and/or secure the rows of opposing folds together. Tool 930 comprises first electrode 933 disposed on first clamp 932 and second electrode 935 disposed on second clamp 934. Tool 930 may, for example, be positioned such that the anterior $R_a$ and posterior $R_p$ rows of tissue folds are clamped between first clamp 932 and second clamp 934. Radiofrequency or other energy then may be delivered across first electrode 933 and second electrode 935 to weld the anterior and posterior rows of tissue folds together. Optionally, solder So may be provided along the region of overlap or contact between the approximated rows of tissue folds in order to facilitate tissue welding. A variety of tissue solders, per se known, may be utilized, e.g., albumin.

Figure 21:
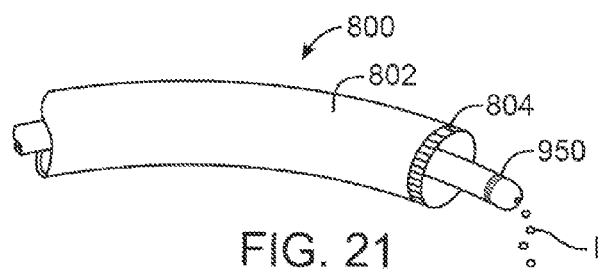
FIG. 21 is a schematic side view of a hemostasis catheter used in combination with the apparatus of 16-19.

Referring now to FIG. 21, apparatus 800 may be used in combination with monopolar, bipolar or multipolar hemostasis catheter 950 advanced through lumen 803 of shaft 802. When utilized in combination with catheter 950, plug mucosectomy optionally may be performed 'hot' or 'cold' (i.e. with or without energizing distal tip 804), and distal tip 804, as well as shaft 802, of apparatus 800 optionally may be electrically insulated. Catheter 950 may be advanced within a plug mucosectomy site and energized to cauterize the site. Optional irrigants I may be injected through the catheter to cool the site during or after electrocautery.

With reference to FIG. 22, interchangeable marking apparatus is described. Apparatus 1000 comprises shaft 1002 having female screw 1004 for attaching and removing interchangeable/exchangeable heads to shaft 1002 for performing various medical procedures. In FIG. 22A, apparatus 1000 further comprises illustrative head 1010 having mating male screw 1012 for mating with female screw 1004 of shaft 1002. As will be apparent, head 1010 alternatively may comprise the female screw and shaft 1002 may comprise the male screw. Furthermore, any alternative mating elements may be provided. Head 1010 illustratively comprises the distal region of apparatus 730 of FIG. 14A. As with apparatus 730, the elongate elements of head 1010 may be energized to ablate tissue.

In FIG. 22B, alternative head 1020 is described comprising mating screw 1022 and the distal region of apparatus 700 of FIG. 11B. FIG. 22C illustrates head 1030 with mating screw 1032 and the cutting element distal region of apparatus 710 of FIG. 13A. In FIG. 22D, head 1040 with mating screw 1042 comprises the distal region of plug mucosectomy apparatus 800 of FIG. 16. Additional exchangeable heads will be apparent.

Referring now to FIG. 23, methods of using additional variations of mucosectomy apparatus to remove mucosal tissue are described. In FIG. 23A, apparatus 1100 comprises tube 1110 having lumen 1111 through which grasper 1120, illustratively corkscrew engagement element 900 that may be screwed into tissue to reversibly engage the tissue, has been advanced. Apparatus 1100 further comprises wire 1130 coupled to the distal end of tube 1110 and configured to pivot thereabout, e.g., via controllable actuation by a medical practitioner external to the patient (see, e.g., FIG. 24).

As shown, grasper 1120 engages and separates mucosal tissue Muc from muscularis tissue Mus. A plug of the engaged mucosal tissue is retracted proximal of wire 1130, which is then pivoted about tube 1110 to sever and separate the plug of tissue from the mucosa, thereby exposing the underlying muscularis, e.g., for the purposes of physical marking, ease of tissue engagement and/or wound healing. Severed tissue optionally may be aspirated or otherwise removed from the patient.

Wire 1130 may comprise a sharpened blade to sever the tissue. Alternatively or additionally, wire 1130 may be electrically coupled to energy source 720 and may be energized to cut through the tissue. To act as a safety mechanism, energizing and pivoting of wire 1130 may be linked, such that wire 1130 is only energized when a medical practitioner pivots the wire.

FIG. 23B provides a variation of apparatus 1100 that illustrates an exemplary technique for removing severed tissue from the patient. In FIG. 23B, "Archimedes" screw pump 1140 is disposed within lumen 1111 of tube 1110. Rotation of screw pump 1140 proximally conveys material disposed within the screw. Thus, severed tissue may be retracted within tube 1110, e.g., via suction or via grasper 1120 (which illustratively is coaxially disposed within a central lumen of the screw pump). Screw pump 1140 then may be rotated to remove the severed material and/or proximally retract the material far enough within lumen 1111 to make room for additional plugs of severed mucosa removed at additional desired locations. Screw pump 1140 optionally may be integrated with corkscrew engagement element 900. Flexible medical devices incorporating screw pumps have previously been described in U.S. Pat. No. 6,156,046 to Passafaro et al., which is incorporated herein by reference in its entirety.

Referring now to FIG. 24, a suction engagement variation of apparatus 1100 is described that does not comprise grasper 1120 or screw pump 1140. Rather, suction may be drawn through lumen 1111 of tube 1110 to engage mucosal tissue, as well as to aspirate tissue severed via wire 1130. A diameter of lumen 1111 may be specified to facilitate engagement of mucosal tissue, but not muscularis tissue.

FIG. 24 also illustrate an exemplary technique for pivoting wire 1130 about tube 1110. As shown, wire 1130 may be distally disposed within rotational bearing 1112 of tube 1110, and may be proximally coupled to elongated member 1132. Elongated member 1132 extends proximally out of the patient from wire 1130 through lumen 1111 of tube 1110. A medical practitioner may advance member 1132 relative to tube 1110 in order to pivot wire 1130 about bearing 1112 and tube 1110. With member 1132 proximally retracted, wire 1130 may be disposed in the delivery configuration of FIG. 24A, while with member 1132 distally extended, wire 1130 may pivot to the deployed tissue-cutting configuration of FIG. 24B.

When wire 1130 is energizable, electrical or other energy impulses may be transmitted from energy source 720 to wire 1130 through elongated member 1132. Member 1132 optionally may be insulated to protect the medical practitioner from, e.g., electrical discharge. Furthermore, distal advancement of member 1132 optionally may activate energy source 720 while proximal retraction of the member may deactivate the energy source.

Referring to FIG. 25, another suction variation of apparatus 1100 is described. In FIG. 25, tube 1110 has been modified, such that lumen 1111 terminates at side aperture 1114 instead of a distal opening. Furthermore, wire 1130 has been formed into a cutting loop that may be advanced and retracted within lumen 1111 via elongated member(s) 1132.

Figure 25A:
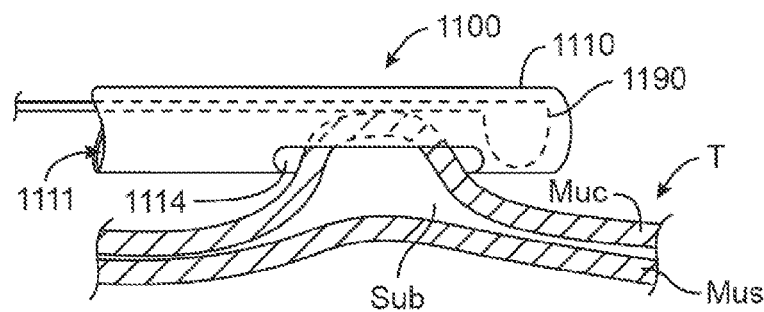
FIGS. 25A and 25B are schematic side views, illustrating a method of using a side-suction engagement variation of the apparatus of FIG. 23 to perform mucosectomy.
Figure 25B:
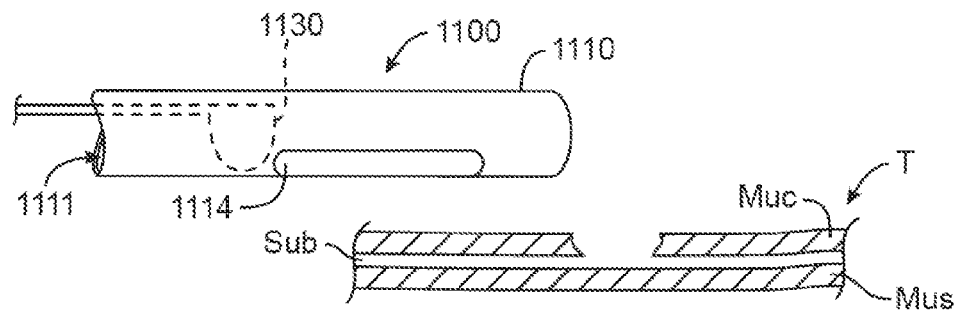

As seen in FIG. 25A, wire 1130 may be advanced distally of side aperture 1114, which may be positioned in proximity to mucosal tissue Muc. Suction then may be drawn through lumen 1111 of tube 1110 to separate a plug of the mucosal tissue from muscularis Mus, with only submucosal tissue Sub disposed therebetween. As seen in FIG. 25B, retracting wire cutting loop 1130 relative to tube 1110 severs the plug of mucosal tissue disposed within lumen 1111. As discussed previously, wire 1130 may be sharpened and/or energized to sever the tissue plug. The severed tissue is then aspirated via suction drawn through lumen 1111. This procedure may be repeated at additional locations, e.g., to map out a GI procedure, to facilitate direct engagement of the muscularis, to initiate a wound healing response, etc.

Figure 26A:
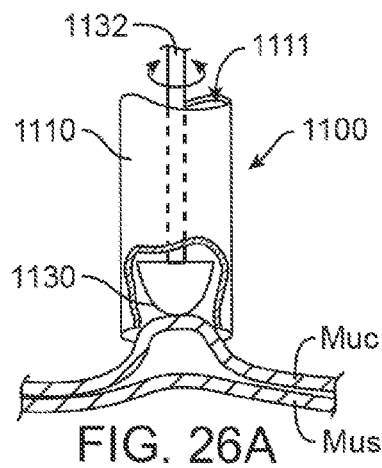
FIGS. 26A and 26B are, respectively, side cut-away and side views, partially in section, illustrating a method of performing mucosectomy with a rotating energizable wire variation of the apparatus of FIG. 23.
Figure 26B:
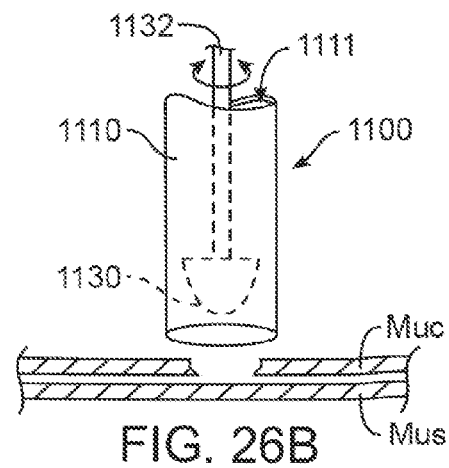

With reference to FIG. 26, yet another suction variation of apparatus 1100 is described. In FIG. 26, lumen 1111 again terminates at a distal opening of tube 1110. Wire 1130 has been formed into an arc coupled to elongated member 1132. Member 1132 is configured for rotation and torque transmission. As seen in FIG. 26A, suction may be drawn through tube 1110 to draw a plug of muscularis Mus within lumen 1111. Wire 1130 contacts the plug of tissue and may be rotated via member 1132 to sever the plug, as seen in FIG. 26B. Member 1132 optionally may be coupled to a motor (not shown) to facilitate rotation. Alternatively, a medical practitioner may manually rotate the member. Wire 1130 may be sharpened and/or energized in order to sever the tissue plug, which then is aspirated via suction drawn through lumen 1111.

Figure 27:
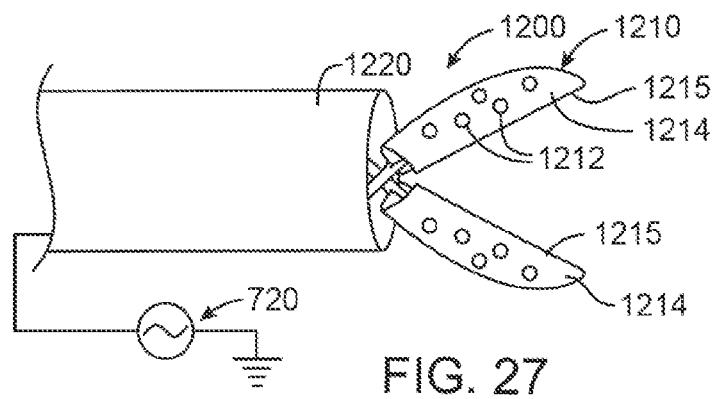
FIG. 27 is a schematic side view of energizable biopsy apparatus comprising suction.

Referring now to FIG. 27, additional mucosectomy apparatus is described. Apparatus 1200 comprises biopsy probe 1210, which has been advanced through lumen 1221 of tube 1220. Probe 1210 comprises aspiration holes 1212. In use, probe 1210 may be advanced against muscularis tissue, and the jaws of the probe may be closed to sever a plug of the tissue. Suction then may be drawn through lumen 1221 of tube 1220, with holes 1212 providing for airflow through probe 1210. This facilitates aspiration of severed mucosal tissue disposed within the probe. Probe 1210 optionally may be energizable, e.g., via coupling to energy source 720. If energized, probe 1210 preferably is only energized along edge 1215 of jaws 1214, thereby enhancing energy density for a given magnitude of energy input.

With reference to FIG. 28, measuring apparatus are described for determining appropriate spacing of tissue markings, e.g., anterior and posterior tissue markings for mapping out endoluminal gastric reduction or partitioning. In FIGS. 28A and 28B, a variation of measuring apparatus 1300 illustratively comprises elongated shaft 1302, anterior ruler 1304 and posterior ruler 1306. The rulers and shaft optionally may be flexible to facilitate endoluminal delivery. Rulers 1304 and 1306 comprise measurement indicia In for measuring distances along the rulers. The rulers are coupled to shaft 1302 of apparatus 1300 at radial bearing 1303 and are configured to rotate about the bearing from the collapsed delivery configuration of FIG. 28A to the expanded deployed configuration of FIG. 28B.

Rulers 1304 and 1306 may also comprise energizable electrodes 1308a and 1308b, which may be energized via energy source 720 in order to mark tissue. A distance D between electrodes 1308a and 1308b in the expanded deployed configuration of FIG. 28B may be specified to provide a desired spacing of tissue markings formed therewith. For example, the electrodes may be spaced such that the spacing between opposing anterior and posterior tissue markings is as desired. As will be apparent, a single electrode or more than two electrodes alternatively may be provided. Furthermore, alternative marking elements may be provided, e.g., ink injection elements, etc.

FIG. 28C provides another variation of apparatus 1300, illustratively disposed in deployed configuration. In the variation of FIG. 28C, apparatus 1300 comprises unitary ruler 1304' rotationally coupled to shaft 1302 at bearing 1303. As with rulers 1304 and 1306, ruler 1304' comprises measurement indicia In and optional electrode or other marking element 1308, illustratively coupled to energy source 720. Ruler 1304' may be cantilevered from a reduced profile delivery and/or retrieval position in line with a longitudinal axis of shaft 1302, to a position out of line with the shaft's longitudinal axis (as in FIG. 28C) for taking measurements and/or marking tissue. Shaft 1302 of apparatus 1300 may be rotated about its longitudinal axis to measure distances with ruler 1304' in any direction perpendicular to the shaft.

Referring now to FIG. 29, a laparoscopic endoluminal method of using another variation of apparatus 1300 to map out endoluminal GI surgery is described. In FIG. 29, bougie 750 has been advanced endoluminally down a patient's throat into the patient's stomach S, and has been positioned along the lesser curvature of the patient's stomach. A variation of apparatus 1300 has been laparoscopically advanced into the patient's stomach in a collapsed delivery configuration, then expanded to the deployed configuration and brought into contact with bougie 750, as seen in FIG. 29A.

As best seen in FIG. 29B, apparatus 1300 may comprise central member 1305 that stabilizes apparatus 1300 against bougie 750 (bougie 750 alternatively may comprise a groove or other surface feature in which apparatus 1300 may be mated, stabilized, etc.). Rulers 1304 and 1306 extend from shaft 1302 towards the anterior An and posterior Po regions of stomach S, respectively. As shown, the rulers may comprise a curvature and/or may be formed from a self-conforming material, such as Nitinol. In this manner, the rulers may approximately follow the curvature of stomach S, thereby providing for more accurate measurements of distance with indicia In.

With rulers 1304 and 1306 properly positioned, optional electrodes 1308 may be energized to physically mark the tissue with markings M. Alternatively, secondary marking apparatus may be utilized to mark the tissue at desired locations, determined, for example, via indicia In. Apparatus 1300 then may be repositioned along the length of bougie 750 in additional planes, where additional anterior and posterior tissue markings may be formed until a desired pattern of markings has been achieved, e.g., opposing anterior and posterior rows of markings. The apparatus then may be collapsed back to the delivery configuration and removed from the patient. Bougie 750 optionally may also be removed.

Figure 30A:
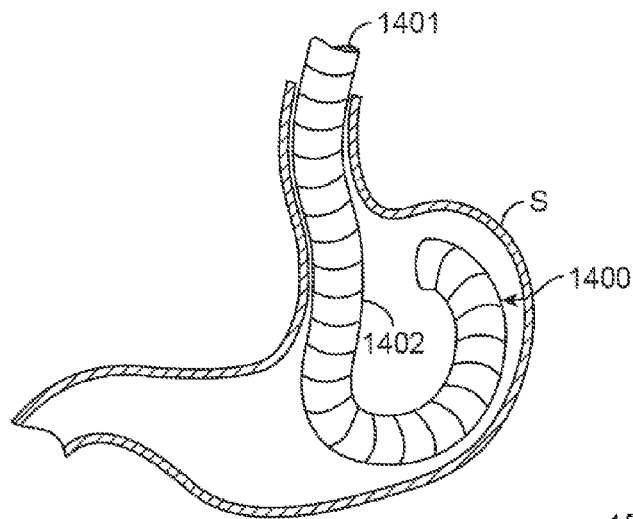
FIGS. 30A and 30B are schematic side views, partially in section, illustrating a fully endoluminal method of using the apparatus of FIG. 29 to map out endoluminal GI surgery.

With reference to FIG. 30, a fully endoluminal method of using apparatus 1300 to map out endoluminal GI surgery is described. In FIG. 30A, steerable endoluminal support 1400 is advanced per-orally into the patient's stomach, and is then retroflexed such that a distal opening of lumen(s) 1401 that extends through the support is positioned facing body 1402 of the support. Steerable endoluminal supports capable of retroflexing are described in more detail in Applicant's U.S. patent application Ser. No. 10/797,485, filed Mar. 9, 2004, which is incorporated herein by reference in its entirety (not shown).

Figure 30B:
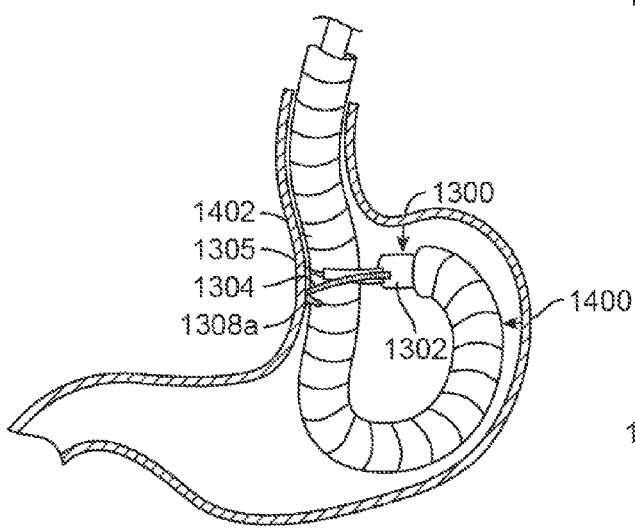

Apparatus 1300 is then advanced through lumen 1401, is expanded to the deployed configuration, and is positioned in contact with body 1402 of support 1400, as in FIG. 30B. In another variation, apparatus 1300 may be attached to a distal region of support 1400. Rulers 1304 and 1306 contact the patient's stomach S along anterior and posterior segments, respectively. Tissue markings may be made, e.g., with electrodes 1308. Then, a degree of retroflexion of endoluminal support 1400 may be altered to reposition apparatus 1300 in a different plane within the patient's stomach wherein additional tissue markings may be made. The procedure may be repeated until a desired pattern of tissue markings have been made for mapping out GI surgery. Apparatus 1300 then may be collapsed back to the delivery configuration within lumen 1401 and may be removed from the patient.

Figure 31A:
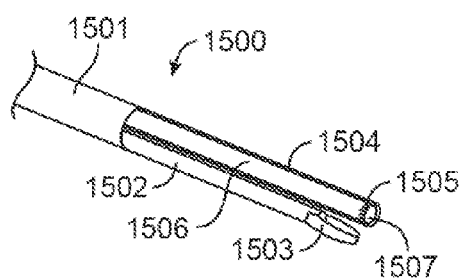
FIGS. 31A and 31B are schematic views of combination measurement and mucosectomy apparatus shown, respectively, in a collapsed delivery configuration and an expanded deployed configuration.
Figure 31B:
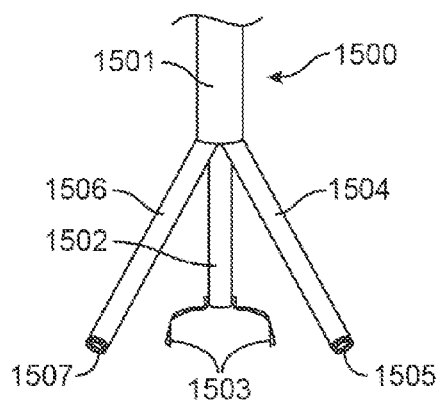

Referring now to FIG. 31, combination measurement and mucosectomy apparatus is described. Apparatus 1500 comprises central shaft 1501 with optional central member 1502 having end region 1503 for stabilizing the apparatus against, e.g., bougie 750. Apparatus 1500 further comprises collapsible anterior and posterior shafts 1504 and 1506, respectively, that extend from shaft 1501. Shafts 1504 and 1506 illustratively comprise optional indicia In for measuring distances within a body lumen, as well as plug mucosectomy tips 1505 and 1507, respectively. Tips 1505 and 1507 are similar to previously described sharpened distal tip 804 of apparatus 800 and are configured to form plug mucosectomies within a patient's stomach. The tips optionally may be energized to ablate, cut or cauterize tissue. FIG. 31A illustrates a collapsed delivery and/or retrieval configuration of apparatus 1500, while FIG. 31B illustrates an expanded deployed configuration.

In use, tips 1505 and 1507 may, for example, be utilized to simultaneously or sequentially form anterior and posterior plug mucosectomies within a patient's stomach. In addition or as an alternative to tips 1505 and 1507, shafts 1504 and 1506 may comprise any previously described or other engagement, marking, ablation, mucosectomy, etc., tips for mapping out or otherwise facilitating endoluminal GI surgery, e.g., for facilitating direct muscularis engagement and/or for initiating a wound healing response. Furthermore, the shafts may comprise tips that perform different functions. For example, one shaft may comprise a grasper for engaging and stabilizing apparatus 1500 against tissue, while the opposing shaft may comprise apparatus for marking tissue or performing mucosectomy. Additional variations will be apparent.

Figure 32:
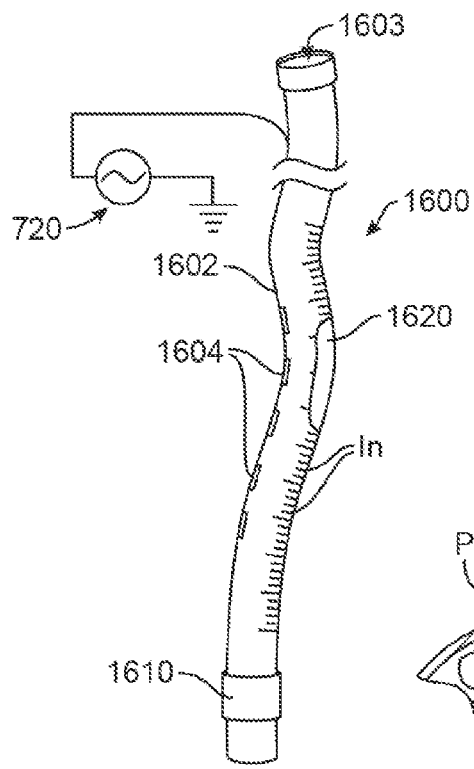
FIG. 32 is a schematic view of centerline marking apparatus.

With reference to FIG. 32, in combination with FIG. 33, centerline marking apparatus 1600 is described. Apparatus 1600 comprises endoluminal support 1602, which may, for example, comprise a bougie or a steerable and/or shape-lockable shaft. Support 1602 comprises a plurality of electrodes 1604 disposed at specified positions with desired spacing along the support. Electrodes 1602 are electrically coupled to energy source 720 to facilitate selective energizing of the electrodes to mark tissue in contact therewith. Support 1602 further optionally may comprise inflatable member 1610 for reversibly engaging a patient's pylorus, as well as measurement indicia In and lumen 1603 with port or slot 1620 in communication with the lumen.

Figure 33A:
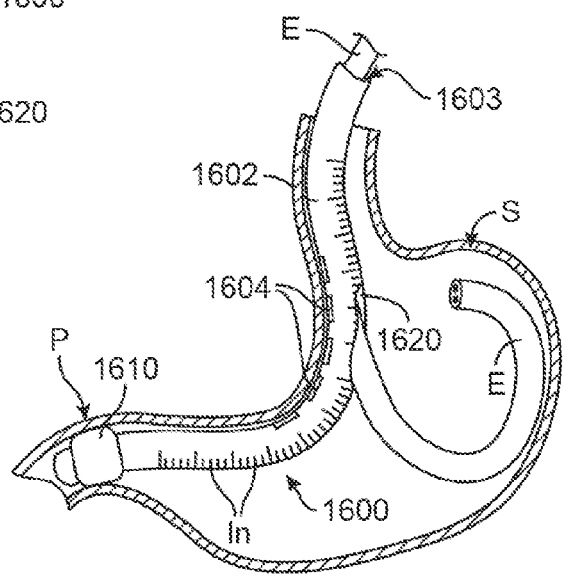
FIGS. 33A and 33B are, respectively, a schematic side view, partially in section, and a schematic rear cut-away view, illustrating a method of using the apparatus of FIG. 32 to mark a centerline within a patient's stomach for mapping out endoluminal GI surgery.
Figure 33B:
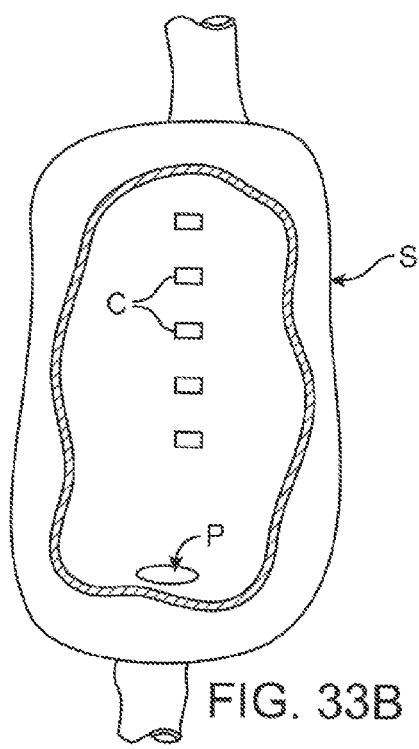

As seen in FIG. 33A, endoluminal support 1602 of apparatus 1600 may be positioned within a patient's stomach S, e.g., along a lesser curvature of the stomach. In one variation, support 1602 may be shape-locked to maintain its position along the lesser curvature. Additionally or alternatively, optional inflatable member 1610 may be positioned within the patient's pylorus P and inflated to reversibly engage the pylorus. Electrodes 1602 then may be energized to form centerline markings C, as seen in FIG. 33B. The centerline markings may provide a reference from which anterior and posterior distances may be measured or determined, and may facilitate partitioning of a patient's stomach, e.g., via formation of anterior and posterior tissue markings and/or tissue folds.

Referring again to FIG. 33A, endoscope E or other instruments optionally may be advanced through lumen 1603 and slot 1620 while endoluminal support 1602 is disposed within the patient's stomach. Endoscope E may, for example, provide visual confirmation that support 1602 is properly positioned for formation of centerline markings C. Methods and apparatus for performing gastroplasty with slotted endoluminal supports are described in greater detail in Applicant's U.S. patent application Ser. No. 10/841,415, filed May 7, 2004, which is incorporated herein by reference in its entirety.

Figure 34A:
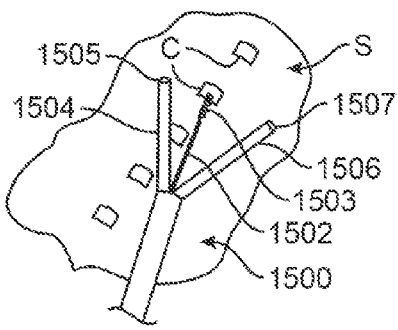
FIGS. 34A and 34B are schematic detail views illustrating a method of using a variation of the apparatus of FIG. 31 in combination with the centerline markings of FIG. 33B to map out endoluminal GI surgery.
Figure 34B:
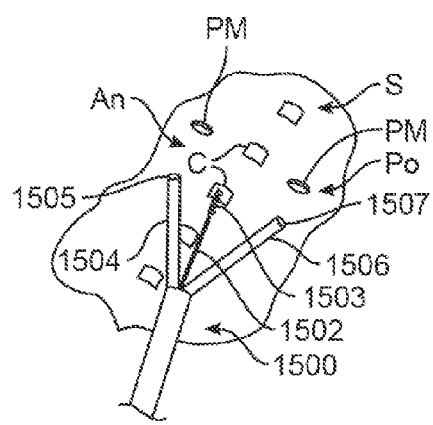

With reference to FIG. 34, a method of using the apparatus of FIG. 31 in combination with the centerline markings of FIG. 33 to map out endoluminal GI surgery is described. As seen in FIG. 34A, a variation of apparatus 1500 is provided comprising central member 1502 with an optional engagement element end region 1503', illustratively a corkscrew grasping element, for engaging a centerline marking C. The positioning of central member 1503 in contact with the centerline orients apparatus 1500 within the patient's stomach. As seen in FIG. 34B, anterior An and posterior Po plug mucosectomies PM may be formed with tips 1505 and 1507 of shafts 1504 and 1506. Apparatus 1500 then may be repositioned along the centerline as shown, e.g., into contact with additional centerline markings C to form additional plug mucosectomies. The spacing of such markings may be specified to facilitate mapping out of endoluminal GI surgeries.

Figure 35:
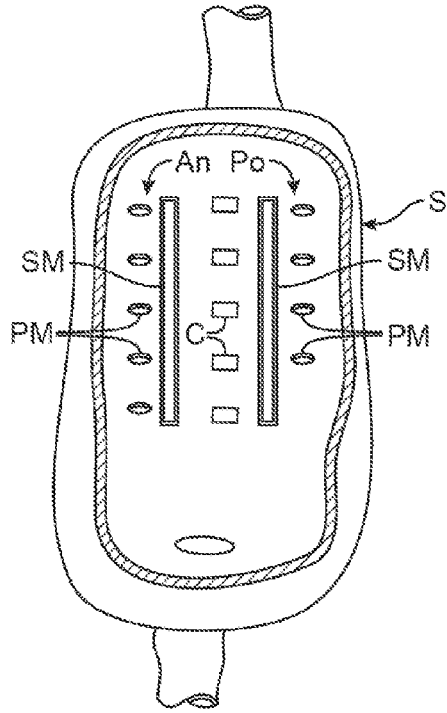
FIG. 35 is a schematic rear cut-away view illustration a method of mapping out endoluminal GI surgery and facilitating direct muscularis engagement through plug mucosectomy, while promoting wound healing response post-surgery through strip mucosectomy.

Referring now to FIG. 35, a method of mapping out endoluminal GI surgery and facilitating direct muscularis engagement through plug mucosectomy, while initiating a wound healing response post-surgery through strip mucosectomy, is described. Centerline markings C may be formed within stomach S, and then opposing rows of anterior An and posterior Po markings may be formed utilizing markings C as a reference, e.g., opposing rows of plug mucosectomies PM may be formed. The anterior and posterior mucosectomies may provide a map of locations whereat a medical practitioner may engage the stomach for forming tissue folds. Furthermore, plug mucosectomies PM advantageously facilitate direct engagement of muscularis tissue, as described previously.

In addition to the plug mucosectomies, opposing anterior and posterior strip mucosectomies SM may be formed between the plug mucosectomies and the centerline markings. A medical practitioner may internally engage the patient's stomach at a plug mucosectomy PM to form a tissue fold, such that the plug mucosectomy is positioned at the top of the fold (i.e., the turning point or critical point of the fold, where the slope of the fold changes direction), and a strip mucosectomy SM forms a side of the fold. Opposing anterior and posterior folds may be formed in this manner and approximated to bring the opposing strip mucosectomies SM into contact. The approximated folds may be secured together in order to partition stomach S and to initiate a wound healing response along the apposed strip mucosectomies SM that in time may fuse them together.

Figure 36A:
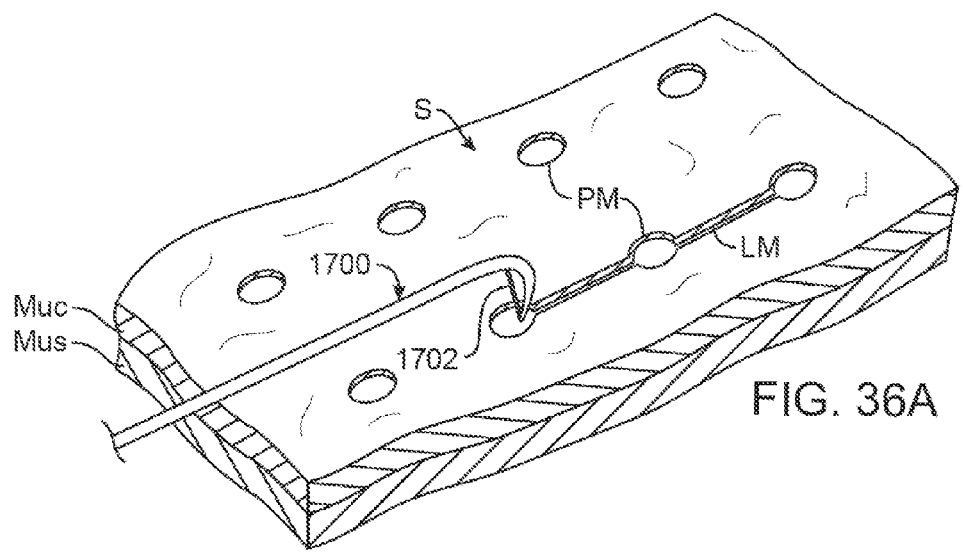
FIGS. 36A and 36B are schematic views illustrating a method and apparatus for forming a strip mucosectomy from a series of plug mucosectomies.
Figure 36B:
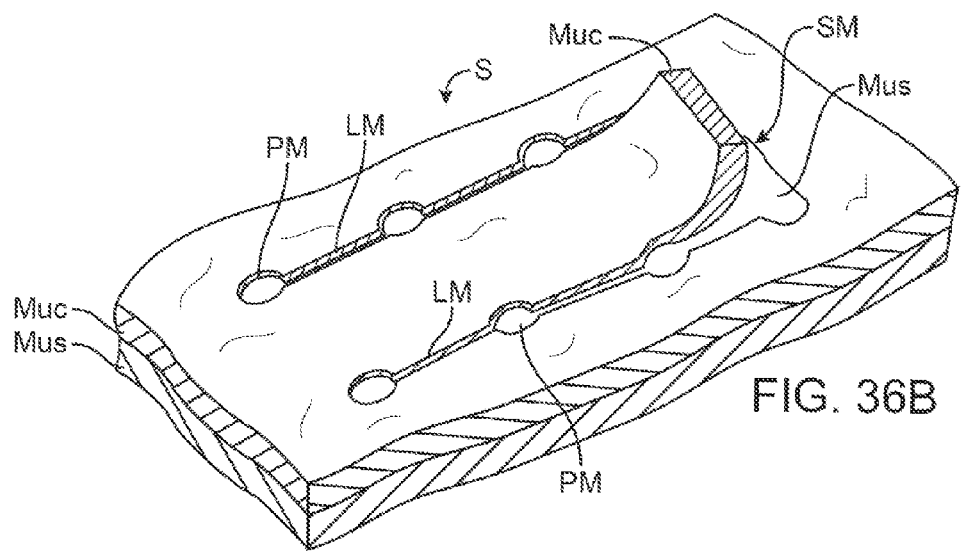

With reference to FIG. 36, a method of forming a strip mucosectomy from a series of plug mucosectomies is described. As seen in FIG. 36A, spaced rows of plug mucosectomies PM may be formed within a patient's stomach S. Hook knife 1700 comprising cutting element 1702, which optionally may be energizable, may be positioned within a plug mucosectomy PM and drawn down to cut away mucosa Muc disposed between the plug mucosectomies, thereby forming line mucosectomy LM. As seen in FIG. 36B, opposing line mucosectomies may be formed along the opposing rows of plug mucosectomies. Then, strip mucosectomy SM may be formed by removing mucosal tissue Muc disposed between the opposing line mucosectomies LM, e.g., by grasping the mucosal tissue and pulling it off, thereby exposing underlying muscularis Mus.

Figure 37:
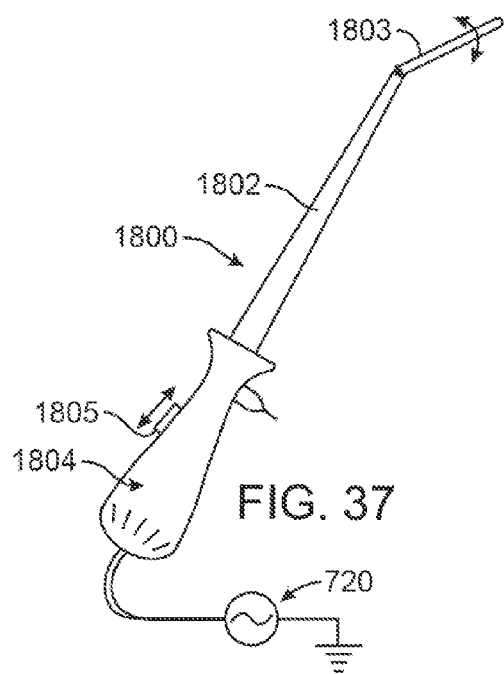
FIG. 37 is a schematic view of additional apparatus for forming a strip mucosectomy.

Referring to FIG. 37, additional apparatus for forming a line or strip mucosectomy is described. Apparatus 1800 comprises shaft 1802 coupled to handle 1804 and having articulating and energizable distal region 1803. Distal region 1803 may, for example, be articulated by actuation of lever 1805 disposed along handle 1804. Distal region 1803 is coupled to energy source 720 for selectively energizing the region. Region 1803 may be positioned against GI tissue at a desired location and energized to ablate and/or remove the mucosa, thereby forming a strip or line mucosectomy. Articulation of region 1803 may facilitate positioning of the region in contact with tissue along its length.

Figure 38A:
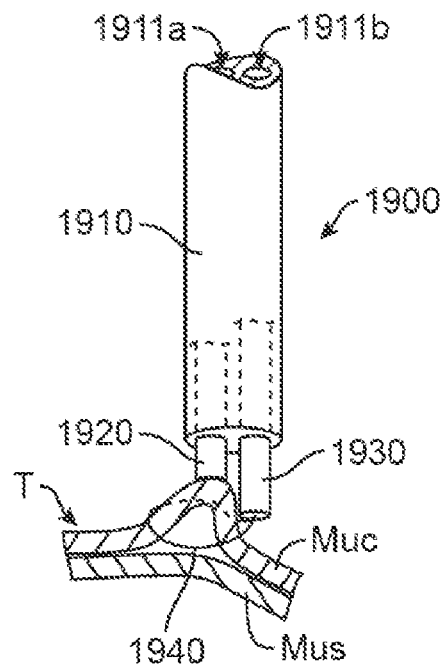
FIGS. 38A and 38B are schematic views of additional variations of apparatus for performing mucosectomy.

With reference to FIG. 38, additional variations of apparatus for performing mucosectomy are described. As seen in FIG. 38A, apparatus 1900 illustratively comprises shaft 1910 having first lumen 1911a and second lumen 1911b. Optional suction tube 1920 has been advanced through lumen 1911a, while optional ligation snare tube 1930 has been advanced through lumen 1911b. Ligation snare 1940 has been advanced through tube 1930 against mucosal tissue Muc. Snare 1940 may, for example, be fabricated from a shape memory material, e.g., Nitinol, such that the snare may resiliently assume a pre-formed bend or other shape to lie adjacent to the mucosal tissue upon exiting tube 1930. Furthermore, the snare may be energizable.

Once properly positioned, suction may be drawn through tube 1920 to capture a plug of mucosal tissue within snare 1940. The snare then may be retracted to cut, sever, ligate, etc., the plug of mucosal tissue disposed therein, thereby facilitating direct engagement of muscularis Mus, mapping of gastrointestinal surgery and/or initiation of a wound healing response. This procedure optionally may be achieved without utilizing tubes 1920 and 1930. In such a variation, suction may be drawn directly through lumen 1911a, and ligating snare 1940 may be advanced directly through lumen 1911b.

Figure 38B:
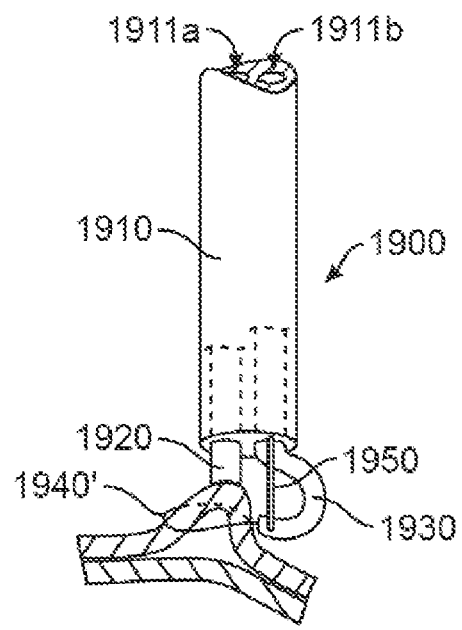

FIG. 38B illustrates a variation of apparatus 1900 wherein ligation snare tube 1930 is pivotably connected to optional support 1950 that extends from the distal region of shaft 1910. Advancement of tube 1930 relative to the shaft and the support may provide tube 1930 with a curvature that facilitates proper placement of snare device 1940' against mucosal tissue Muc. As shown, snare device 1940' does not comprise a pre-formed bend and may be advanced through tube 1930 while the tube is disposed parallel to the mucosa.

Figure 39A:
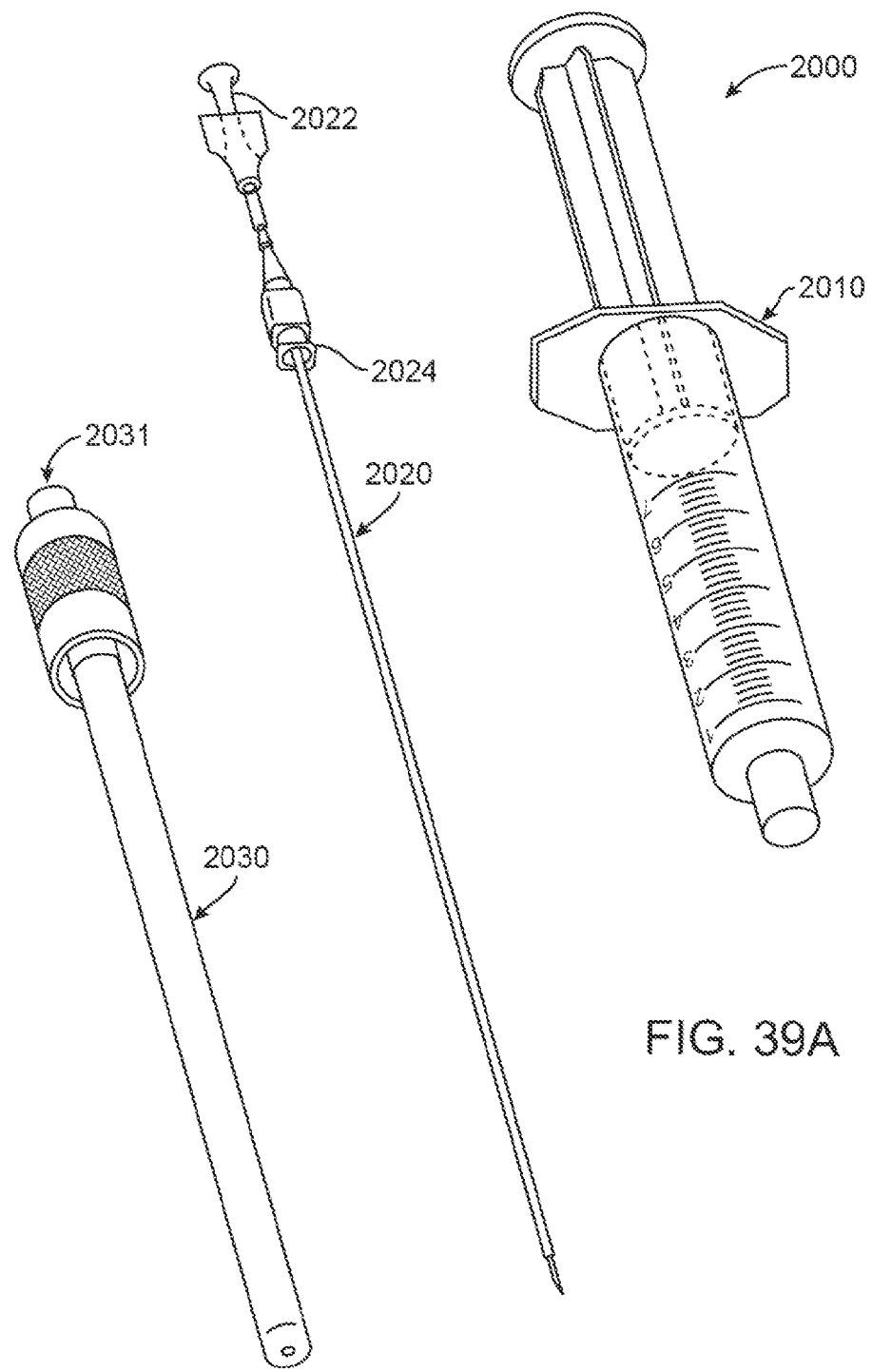
FIGS. 39A and 39B are exploded and assembly views, respectively, of another variation of apparatus for performing tissue marking and/or mucosectomy.
Figure 39B:
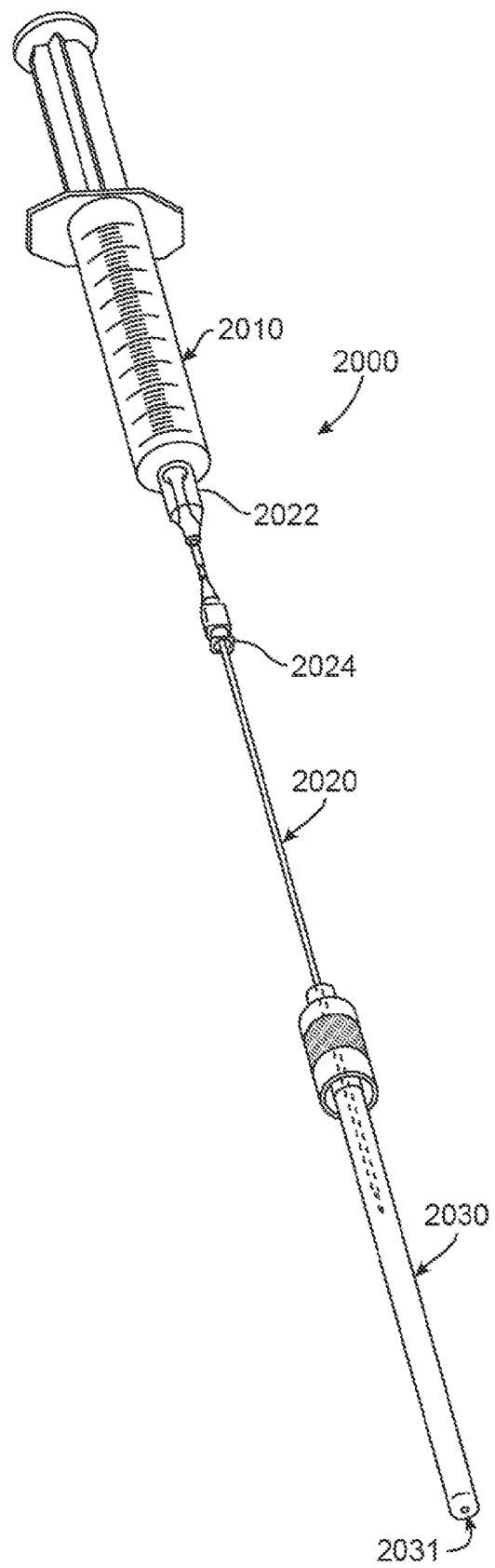

Referring now to FIG. 39, another variation of apparatus for performing tissue marking and/or mucosectomy is described. As seen in FIG. 39A, apparatus 2000 comprises syringe 2010, needle 2020 and overtube 2030. Needle 2020 comprises syringe attachment 2022 and overtube attachment 2024. Overtube 2030 having lumen 2031 may comprise, for example, a substantially rigid laparoscopy trocar or, alternatively, a flexible endoluminal overtube. As seen in FIG. 39B, needle 2020 may be coupled to syringe 2010 via syringe attachment 2022 and may be advanced through lumen 2031 of overtube 2030. Additionally, needle 2020 optionally may be coupled to overtube 2030 via overtube attachment 2024.

With reference to FIG. 40, a method of utilizing the apparatus of FIG. 39 to separate mucosal tissue from underlying muscularis tissue is described. As seen in FIG. 40A, the sharpened distal tip of needle 2020 may be advanced into submucosa Sub between mucosa Muc and muscularis Mus. A distance that needle 2020 extends beyond a distal end of overtube 2030 may act as a depth-limiting element to ensure that the needle is not inadvertently advanced into the muscularis. As seen in FIG. 40B, a fluid, such as air, saline, dye, etc., may be injected through syringe 2010 and needle 2020 into the submucosal space to form fluid bolus Bo that separates mucosa Muc from muscularis Mus. Bolus Bo may provide a visually identifiable tissue marking and/or may facilitate mucosectomy, e.g., via a snare device.

Figure 41:
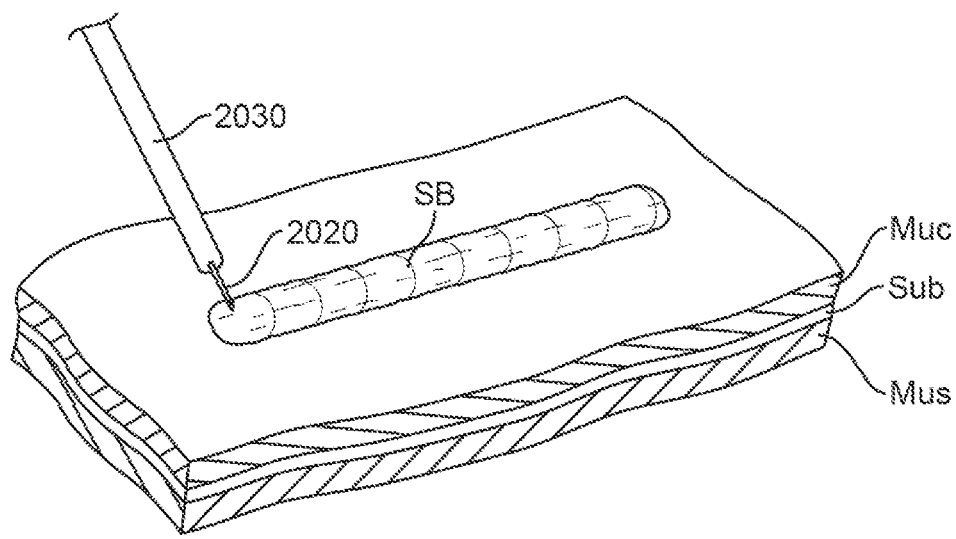
FIG. 41 is a schematic view illustrating a method of separating mucosal tissue from underlying muscularis tissue along a line.

Referring now to FIG. 41, needle 2020 may be repositioned to additional locations in order to separate the muscularis and mucosal tissue at a plurality of desired locations and/or in any desired shape or configuration. In FIG. 41, illustrative strip bolus SB is formed by forming a plurality of boluses along a line. This may facilitate optional formation of a strip mucosectomy.

Although preferred illustrative embodiments of the present invention are described hereinabove, it will be apparent to those skilled in the art that various changes and modifications may be made thereto without departing from the invention. For example, a variety of energy sources optionally may be utilized to mark or otherwise manipulate tissue, including, but not limited to lasers (pulsed or continuous), RF (monopolar, bipolar or multipolar), high energy ultrasound, etc. It is intended in the appended claims to cover all such changes and modifications that fall within the true spirit and scope of the invention.

What is claimed is:

1. A method for directly engaging muscularis tissue from an interior of a patient's stomach, the method comprising:
   removing plugs of mucosal tissue from opposing anterior and posterior segments of the interior of the patient's stomach to expose underlying muscularis tissue;
   engaging the exposed underlying muscularis tissue along the opposing anterior and posterior segments; and forming opposing tissue folds along the opposing engaged segments of muscularis tissue.

2. The method of claim 1, wherein removing plugs of mucosal tissue further comprises removing the mucosal tissue at desired locations to form physical markings, thereby mapping out endoluminal gastrointestinal surgery.

3. The method of claim 2, wherein mapping out endoluminal gastrointestinal surgery further comprises mapping out endoluminal gastric reduction.

4. The method of claim 1, wherein removing plugs of mucosal tissue further comprises mechanically cutting the mucosal tissue.

5. The method of claim 1, wherein removing plugs of mucosal tissue further comprises ablating the mucosal tissue.

6. The method of claim 1 further comprising aspirating removed plugs of mucosal tissue from the patient's stomach.

7. The method of claim 1 further comprising cauterizing mucosal tissue that has not been removed to stanch bleeding.

8. The method of claim 7, wherein cauterizing further comprises electrocauterizing.

9. The method of claim 1 further comprising approximating the opposing tissue folds to partition the patient's stomach.

10. The method of claim 9 further comprising initiating a wound healing response along one or more points of contact between the approximated opposing tissue folds.

11. The method of claim 10, wherein initiating a wound healing response comprises removing mucosal tissue along the one or more points of contact.

12. The method of claim 10, wherein initiating a wound healing response comprises ablating mucosal tissue along the one or more points of contact.

13. The method of claim 9 further comprising welding the approximated opposing tissue folds together along one or more points of contact between the approximated folds.

14. The method of claim 13, wherein welding the approximated opposing tissue folds together further comprises placing a tissue solder along the one or more points of contact.

15. The method of claim 14, wherein welding the approximated opposing tissue folds together further comprises heating the tissue solder.

16. The method of claim 1, wherein removing plugs of mucosal tissue along opposing anterior and posterior segments further comprises determining locations for mucosal tissue removal by specifying distances between the anterior and posterior segments.

17. The method of claim 16, wherein specifying distances further comprises measuring the distances.

18. The method of claim 1, wherein forming opposing tissue folds along the opposing engaged segments further comprises forming opposing rows of tissue folds along the opposing engage segments.

19. The method of claim 18 further comprising approximating the opposing rows of tissue folds to partition the patient's stomach.

20. The method of claim 1, wherein removing plugs of mucosal tissue further comprises separating the mucosal tissue from the underlying muscularis tissue prior to removal of the mucosal tissue.

21. The method of claim 20, wherein separating the mucosal tissue from the underlying muscularis tissue further comprises injecting a bolus of fluid into a submucosal space between the mucosal tissue and the muscularis tissue.

22. A method for directly engaging muscularis tissue from an interior of a patient's stomach, the method comprising:
   separating mucosal tissue from underlying muscularis tissue on opposing anterior and posterior segments of the interior of the patient's stomach;
   removing the separated mucosal tissue to expose the underlying muscularis tissue;
   engaging the exposed underlying muscularis tissue along the opposing anterior and posterior segments; and
   forming opposing tissue folds along the opposing engaged segments of muscularis tissue.

23. The method of claim 22, wherein separating the mucosal tissue from the underlying muscularis tissue further comprises injecting a bolus of fluid into a submucosal space between the mucosal tissue and the muscularis tissue.

* * * * *